US007625728B2

(12) United States Patent
Eroma et al.

(10) Patent No.: US 7,625,728 B2
(45) Date of Patent: Dec. 1, 2009

(54) PROCESS FOR THE SIMULTANEOUS PRODUCTION OF XYLITOL AND ETHANOL

(75) Inventors: Olli-Pekka Eroma, Kotka (FI); Heikki Heikkila, Espoo (FI); Heikki Ojamo, Lohja (FI); Päivi Sarmala, Kantvik (FI); Göran Hyöky, Askainen (FI); Leena Rahkila, Kauniainen (FI); Marja-Leena Sarkki, Kantvik (FI); Tapio Viljava, Kantvik (FI)

(73) Assignee: Danisco Sweeteners Oy, Espoo (FI)

( * ) Notice: Subject to any disclaimer, the term of this patent is extended or adjusted under 35 U.S.C. 154(b) by 364 days.

(21) Appl. No.: 11/479,654

(22) Filed: Jun. 30, 2006

(65) Prior Publication Data

US 2006/0246563 A1 Nov. 2, 2006

Related U.S. Application Data

(60) Division of application No. 10/035,476, filed on Oct. 25, 2001, now Pat. No. 7,109,005, which is a continuation-in-part of application No. 08/928,893, filed on Sep. 12, 1997, now Pat. No. 6,846,657, which is a continuation of application No. 07/910,133, filed on Jul. 14, 1993, now abandoned.

(30) Foreign Application Priority Data

Jan. 15, 1990 (FI) ...................................... 900220

(51) Int. Cl.
C12P 7/18 (2006.01)
C12P 7/06 (2006.01)
C12P 7/08 (2006.01)
C12P 7/10 (2006.01)
C12N 1/16 (2006.01)

(52) U.S. Cl. ........................ 435/158; 435/105; 435/161; 435/163; 435/165; 435/255.4; 435/255.5; 435/255.7; 435/911; 435/921; 435/924

(58) Field of Classification Search ........................ None
See application file for complete search history.

(56) References Cited

U.S. PATENT DOCUMENTS

| 2,684,331 | A | 7/1954 | Bauman |
| 2,911,362 | A | 11/1959 | Wheaton |
| 2,985,589 | A | 5/1961 | Broughton et al. |
| 3,586,537 | A | 6/1971 | Steiner et al. |
| 3,619,369 | A | 11/1971 | Onishi et al. |
| 3,627,636 | A | 12/1971 | Jaffe et al. |
| 3,784,408 | A | 1/1974 | Jaffe et al. |
| 3,928,193 | A | 12/1975 | Melaja et al. |
| 4,008,285 | A | 2/1977 | Melaja et al. |
| 4,066,711 | A | 1/1978 | Melaja et al. |
| 4,075,406 | A | 2/1978 | Melaja et al. |
| 4,096,036 | A | 6/1978 | Liu et al. |
| 4,368,268 | A | 1/1983 | Gong |
| 4,471,114 | A | 9/1984 | Sherman et al. |
| 4,631,129 | A | 12/1986 | Heikkilä |
| 4,857,642 | A | 8/1989 | Kulprathipanja |
| 4,940,548 | A | 7/1990 | Zinnen |
| 4,990,259 | A | 2/1991 | Kearney et al. |
| 5,047,332 | A | 9/1991 | Chahal |
| 5,081,026 | A | 1/1992 | Heikkila et al. |
| 5,122,275 | A | 6/1992 | Rasche |
| 5,127,957 | A | 7/1992 | Heikkila et al. |
| 5,177,008 | A | 1/1993 | Kampen |
| 5,198,120 | A | 3/1993 | Masuda et al. |
| 5,225,580 | A | 7/1993 | Zinnen |
| 5,536,526 | A | 7/1996 | Virtanen et al. |
| 5,616,361 | A | 4/1997 | Virtanen et al. |
| 5,637,225 | A | 6/1997 | Heikkilä et al. |
| 5,951,777 | A | 9/1999 | Nurmi et al. |

FOREIGN PATENT DOCUMENTS

| EP | 0 279 946 A2 | 8/1988 |
| EP | 0 279 946 A3 | 8/1988 |
| EP | 0 279 946 B1 | 8/1988 |
| EP | 0 345 511 A2 | 12/1989 |
| EP | 0 345 511 A3 | 12/1989 |
| EP | 0 345 511 B1 | 12/1999 |
| FR | 2641545 | 7/1990 |
| JP | 632 19 386 | 9/1988 |
| JP | 64-080409 | 3/1989 |
| WO | WO 88/05467 | 7/1988 |
| WO | WO 90/06796 | 6/1990 |
| WO | WO 90/08193 | 7/1990 |
| WO | WO 91/08815 | 6/1991 |

OTHER PUBLICATIONS

Publication: *"Biotechnological Production of Xylitol. Part 3: Operation In Culture* Media Made From Lignocellulose Hydrolysates", by Juan Carlos Parajo, Herminia Domiquez & Jose Manuel Dominguez of Department of Chemical Engineering, University of Vigo, Ourense, Spain, published by *Bioresource Technology* 66 (1998), pp. 25-40.

Publication: *"Fermentation of Lignocellulosic Hydrolysates For Ethanol Production"*, by Lisbeth Olsson and Barbel Hanh Hagerdal of Applied Microbiology, University of Lund/Lund Institute of Technology, Lund Sweden, published by *Enzyme and Microbial Technology* 18: pp. 312-331, (1996).

(Continued)

Primary Examiner—David M Naff
(74) Attorney, Agent, or Firm—Kenyon & Kenyon LLP

(57) ABSTRACT

Effective processes are provided for the production of xylitol and ethanol and other products from solutions derived from lignocellulose-containing material in biomass. The solutions can be hydrolyzed or partially hydrolyzed before being fermented with microbes. The fermented solution can be distilled and can be subsequently separated, such as, by chromatographic separation, membrane separation, etc. The recovered xylitol solution can be crystallized to provide pure xylitol crystals.

19 Claims, 6 Drawing Sheets

OTHER PUBLICATIONS

Publication: "*Alternative Sweeteners Second edition, revised and Expanded*", by Albert Bar, Bioresco Ltd., Brussels, Belgium, edited by Lyn O'Brien Nabors and Robert C. Gelardi of Calorie Control Council, Atlanta, Georgia, published by *Marcel Dekker, Inc.* pp. 349-379 (1991).

Abstract: Japanese Application No. 59-183571 filed Aug. 31, 1984, Publication No. 61-063291 (1063291), published Apr. 1, 1986 of Dai Ichi Kogyo Seiyaku Co., Ltd. pertains to the Production of Xylitol Through Enzymatic Process.

Abstract: Japanese Application No. 60-244968 filed Oct. 30, 1985, Publication No. 62-104588 (2104588), published May 15, 1987 of Nitto Electric Ind. Co., Ltd., pertains to Production of Xylitol.

Abstract: Japanese Application No. 59-1411 filed Jan. 10, 1984, Publication No. 60-145095 (0145095), published Jul. 31, 1995 of Jiyuujiyou Seishi KK, pertains to Preparation of Xylitol By Immobilized Microorganism.

Abstract: Japanese Publication No. 45-24834 (0024834), published Aug. 18, 1970 of Zaidan Hojin Noda Sangyak (Zaid), pertains to Production Of Xylitol By Fermentation.

Lohmeier-Vogel, Elke et al., "Shifting Product Formation from Xylitol to Ethanol in Pentose Fermentation with Candida tropicalis by Altering Environmental Parameters", Annals New York Academy of Sciences, pp. 152-154 1984.

Jeffries, T.W., "Enzymatic Removal and Utilization of Hemicellulose from Pulps", Abstract of Papers—American Chemical Society, Aug. 26-31, 1990, (Abstract 55).

Converti, Attilio et al., "Xylitol Production from Hardwood Hemicellulose Hydrolysates by Pachysolen tannophilus, Debaryomyces hansenii, and Candida guilliermondii", Applied Biochemistry and Biotechnology, vol. 82, 1992 pp. 141-151.

Converti, A. et al., "Selection of Hemicellulosic Hydrolysate Pretreatments and Fermentation Conditions to Stimulate Xylitol Production by Ethanol-Producing Yeasts", Acta Biotechnol. 16, vol. 16, 1996, pp. 133-144.

Latif, Farooq et al., "Production of Ethanol and Xylitol from Corn Cobs by Yeasts", Bioresource Technology 77, 2001, pp. 57-63.

Perego, Patrizia et al., "Fermentation of Hardwood Hemicellulose Hydrolysate by Pachysolen tannophilus, Candida shehatae and Pichia stipitis", Journal of Industrial Microbiology, 6, 1990, pp. 157-164.

Walthers, Thomas et al., "Model Compound Studies: Influence of Aeration and Hemicellulosic Sugars on Xylitol Production by Candida tropicalis", Applied Biochemistry and Biotechnology, vol. 91-93, 2001, pp. 423-435.

Onishi et al., "The Production of Xylitol L-Arabinitol and Ribitol by Yeasts", Agr. Biol. Chem., vol. 30, No. 11, 1966, pp. 1139-1144.

Chemical Abstract No. 34371t, "Utilization of the Hemicellulosic Fraction of Agro Industrial Residues by Yeasts", vol. 112, 1990, p. 449.

Chemical Abstract No. 177464d, "Bioconversion of Hemicellulose: Aspects of Hemi Cellulase Production", vol. 98, 1983, p. 504.

Chemical Abstract No. 41196y, "Xylose Fermentation by Candia shehatae and Pichia stipitis: Effects of pH, Temperature and Substrate Concentration," vol. 105, No. 5, Aug. 1986, p. 604.

Chemical Abstracts, vol. 105, No. 5, Aug. 4, 1986, (Columbus, Ohio, US), J. C. Du Preez et al.: "Xylose fermentation by Candida shehatae and Pichia stipitis: effects of pH, temperatue and substrate concentration":, see p. 604, Abstract 41196y, & Enzyme Microb. Technol., 8(6), 360-364(1986).

Chemical Abstracts, vol. 112, No. 5, Jan. 29, 1990, (Columbus, Ohio, US), M.T. Amaral-Collaco et al.: Utilization of the hemicellulosic fraction of agro-Industrial residues by yeasts:, see p. 449, Abstract 34371t, & Enzyme Syst. Lignocellul. Degrad., 221-230 (1989).

Chemical Abstracts, vol. 114, No. 5, Feb. 4, 1991, (Columbus, Ohio, US), K.B. Taylor et al.: "The fermentation of xylose: studies by carbon-13 nuclear magnetic resonance spectroscopy", see p. 592, Abstract 41014y, & J. Ind. Microbiol., 6 (1), 29-41 (1990).

Chemical Abstract, vol. 98, No. 9, Feb. 28, 1983, (Columbus, Ohio, US), Gong, Cheng Shung et al.: Conversion of pentoses by yeasts:, see p. 484, Abstract 70314c, & Biotecnol. Bioeng., 25(1), 85-102 (1983).

Publication: "Third European Congress On Biotechnology", by Weinheim presented in Muchen, Federal Republic of Germany, vol. II (Sep. 10-14, 1984).

Publication: "*Chromatography of Oligosaccharides and Related Compounds on Ion-Exchange Resin*" by Department of Engineering Chemistry, Chalmers University of Technology, Goteborg, Sweden, Advances in Chromatography, vol. 16, pp. 113-149 (1978).

Publication: "The Distribution of Polyalcohols Between Organic Ion Exchangers and Water" by Matte Mattisson and Olof Samuelson, Department of Engineering Chemistry, Chalmer Tekniska Hogskola, Goteborg, Sweden, No. 7, pp. 1386-1394 (1958).

Publication: "*Ion-Exchange Chromatography of Aldehydes, Ketones, Ethers. Alcohols, Polyols and Saccharids*" published in Journal of Chromatographprinted by Chromatographic Reviews, Elsevier Scientific Publishing Company, Amsterdam-Printed in The Netherlands, 98 pp. 55-104 (1974).

Publication: "*Xylitol dehydrogenase from Pachysolen tannophilus*" by G. Ditzelmuller, C.P. Kubicek, W. Wohrer and M. Rohr of Institute for Biochemische Technologie and Mikrobiolgies, Wien, Austria, pp. 195-198 (Jul. 31, 1984).

Abstract: French Application No. FR19890000209 filed Jan. 10, 1989, Publication No. FR2641545 published Jul. 13, 1990 of Agrocinq pertains to a Process For The Biosynthesis of Xylitol.

Abstract: Japanese Application No. 62-235014 filed Aug. 21, 1987, Publication No. 64-080409 published Mar. 27, 1989 of Japan Organo Co., Ltd. pertains to a False Moving Bed Device.

Publication: "Fermentation of Cellulose and Hemicellulose Carbohydrates by Thermotolerant Yeasts" by Linda D. McCracken and Cheng-Shung Gong of Laboroatory of renewable Resources Engineering, A.A. Potter Engineering Center, Purdue University, West Lafayette, Indiana, published by Biotechnology and Bioengineering Symp. No. 12, 91-102 (1982).

Publication: "Conversion of D-Xylose Into Xylitol by Xylose Reductase From Candida Pelliculose Coupled With the Oxidoreductase System of Methanogen Strain HU" by V. Kitpreechavanich of Department of Microbiology, M. Hayasi, N. Nishio and S. Hagai of Department of Fermentation Technology, published Biotechnology Letter, vol. 6 No. 10, pp. 651-656 (1984).

Publication: "Quantitative Production of Xylitol From D-Xylose By a High-Xylitol Producing Yeast Mutant Candida tropicalis HXP2" by Cheng-Shung Gong, Li Fu Chen and George T. Tsao of Laboratory of Renewable Resources Engineering, A.A. Potter Engineering Center, Purdue University, West Lafayette, Indiana, published in Biotechnology Letters vol. 3 No. 3, pp. 130-135 (1981).

Chem. Abstracts, vol. 105, No. 5, Aug. 4, 1986, J.C. Du Preez et al,: "Xylose fermentation by Candida shehatae and Pichia stipitis: effects of pH, temperature and substrate concentration", p. 604, abstract 41196y** & Enzyme Microb. Technol. 1986 8(6), 360-364.

Chem. Abstracts, vol. 112, No. 5, Jan. 29, 1990, M.T. Amaral-Collaco et al.: "Utilization of the hemicellulosic fraction of agro-industrial residues by yeasts", p. 449, abstract 3437t**, & Enzyme Syst. Lignocellul. Degrad. 1989, (), 221-230.

Chem. Abstracts, vol. 114, No. 9, Feb. 4, 1991, K.B. Taylor et al.: "The fermentation of xylose: studies by carbon13 nuclear magnetic resonance spectroscopy", p. 592, abstract 41014y**, IJ. Ind. Microbiol. 1990, 6 (1), 29-41.

Chem. Abstracts, vol. 98, No. 9, Feb. 28, 1983, Gong, Cheng Shung et al.: "Conversion of pentoses by yeasts", p. 484, abstract 70314c**, & Biotechnol. Bioeng. 1983, 25 (1), 85-102.

International Search Report PCT/FI 91/00011, 1991.

Dorfner, K., Ion Exchangers, Properties and Applications, Ann Arbor Science Publisher Inc., pp. 44-45, 1997.

Duolite C 464, Weak Acid Cation Exchange Resin, Feb. 1981, 3 pages.

Zaborsky, O., Immobilized Enzymes, CRC Press, pp. 5-27, 1973.

Sax, N. and Lewis, Sr., R., Hawley's Condensed Chemical Dictionary, 11th ed., pp. 15 and 893, 1987.

Morrison, R. and Boyd, R., Organic Chemistry, 5th ed., pp. 833 and 839, 1992.

Allenza, P., Scherl, D., and Detroy, R., Hydrolysis of Xylan by an Immobilized Xylanase from *Aureobasidium pullulans*, Biotechnology and Bioengineering Symp. No. 17 (1986) pp. 425-433.

Jenq, C.Y., Wang, S.S. and Davidson, B., Ultrafiltration of Raw Sewage Using an Immobilized Enzyme Membrane, Enzyme Microb. Technol., Apr. 1980, vol. 2, pp. 145-147.

Dekker, Robert F.H., Bioconversion of Hemicellulose: Aspects of Hemi-cellulase Production by Trichoderma reesei QM 9414 and Enzyme Saccharification of Hemicellulose, Abstract 177464d, Chemical Abstracts, vol. 98, 1983.

Weckstrom, L. and Leisola, M., Enzymatic Hydrolysis of Hemicellulose From Bisulfite Waste, Proc. Int. Ferment. Symp., 1981, vol. 2, pp. 21-26.

Poutanen, K. And Puls, J., Enzymatic Hydrolysis of Steam-Pretreated Lignocellulosic Materials, Third European Congress on Biotechnology, vol. 11, Sep., 1984, pp. 217-223.

International Preliminary Examination Report for PCT/FI91/00011 and Official Action for Fi 900220.

International Search Report for PCT/F190/00015.

Hyrkas et al., Heran Laktoosin Hydrolyysi Immobilisoidulla ÿ-Galaktosidaasilla, 1974, pp. 38-47 and English language summary and translation of abstract.

Horitsu H: Sugar Alcohol Prepn. by Treating Mixed Sugar Soln. Cong. Substrate Sugar and Hydrogen Donor Sugar with Candida Yeast, Dialog Information Services, File 351, WPI 81-90, Dialog Accession No. 88-297740/42.

Amaral-Collaco, et al., Utilization of the Hemicellulosic Fraction of Agro Industrial Residues by Yeasts, Abstract 34371t, Fermentations vol. 112, 1990.

Onishi et al., The Production of Xylitol, L-Arabinitol and Ribitol by Yeasts, Agr. Biol. Chem., vol. 30, No. 11, 1996, pp. 1139 and 1144.

WecKstrom, L. and Leisola, M., Enzymatic Hydrolysis of Hemicellulose From Bisulfite Waste, Abstract 96:124760z, Wood Products, vol. 96, 1982.

PROCESS FOR THE SIMULTANEOUS PRODUCTION OF XYLITOL AND ETHANOL

RELATED APPLICATIONS

This Application is a divisional of U.S. Ser. No. 10/035,476, filed Oct. 25, 2001 now U.S. Pat. No. 7,109,005, which is a continuation-in-part (CIP) of U.S. Ser. No. 08/928,893 filed Sep. 12, 1997, now U.S. Pat. No. 6,846,657, which is a continuation of U.S. Ser. No. 07/910,133 filed Jul. 14, 1993, now abandoned, the entire disclosures of which are hereby incorporated by reference.

BACKGROUND OF THE INVENTION

The present invention relates to a process for the production of xylitol and/or ethanol from lignocellulose-containing material.

Xylitol is a naturally occurring sugar alcohol which is formed in the reduction reaction of xylose and which corresponds to "normal" sugar in sweetness and low in caloric content (i.e. 2.4 kcal/g). Xylitol is found in small quantities in many fruits and vegetables and is also produced in the human body as a normal metabolic product. Xylitol is a very good special sweetener in different connections on account of its certain metabolic, dental and technical properties. Desirably, the xylitol metabolism is independent of the insulin metabolism, and therefore also diabetics can use xylitol. Xylitol also has a retarding effect on the bowel and may have utility in reducing diets. Furthermore, it has been found that xylitol does not cause caries but has a anti-cariogenic effect.

Despite the many advantages of xylitol, its use has been rather restricted. The reason for this is the relatively high price of xylitol, which in turn is a result of the difficulties of producing xylitol on a larger scale.

Xylitol has earlier been produced from xylan-containing materials by hydrolysis, in which process a monosaccharide mixture containing e.g. xylose is obtained. Xylose is then converted to xylitol, generally in the presence of a nickel catalyst, such as Raney nickel. A number of processes for the production of xylose and/or xylitol from a xylan-containing material have been described in the literature in this field. As examples may be mentioned U.S. Pat. No. 3,764,408 (Jaffe at al.), U.S. Pat. No. 4,066,711 (Melaja at al.), U.S. Pat. No. 4,075,406 (Melaja at al.), U.S. Pat. No. 4,008,285 (Melaja at al.) and U.S. Pat. No. 3,586,537 (Steiner at al.).

These prior processes are all multi-step processes which are relatively costly and often have inadequate efficiency. The greatest problems reside in the effective, high yield separation of xylose and/or xylitol from polyols and other hydrolysis and conversion products and the use of the by-products which are produced in large quantities in the process. Purification of the preceding can be very exacting because catalysts used in the reduction reaction of xylose are very sensitive. The purity of the final product often depends on the extent that the xylitol can be separated from the other products produced in the reduction reaction.

It is known that several yeast strains produce reductase enzymes which catalyze the reduction of sugars into corresponding sugar alcohols. Certain Candida strains have been reported to produce xylitol from xylose (Dtzelmullez, G. at al.: *FEMS Microbiology Letters* 25 (1985), pp. 195-198, Kitpreechavanich, M. at al.: *Biotechnology Letters Vol.* 6 (1984), pp. 651-656, Gong, C-S. at al.: *Biotechnology Letters Vol.* 3 (1981), pp. 130-135). However, these studies have been carried out on a laboratory scale only, and the literature in this field has not disclosed processes wherein pure xylitol is separated from the fermentation product.

The Applicants' copending U.S. patent application Ser. No. 297,791 filed on Jan. 17, 1989, now U.S. Pat. No. 5,081,026, and published as WO-A-9008193, describes a process for the production of pure xylitol from plant material using chromatographic separation following hydrolysis and fermentation. However, in this process the majority of the raw material can be lost as a worthless waste material. If a greater part of the raw materials could be converted to commercial products, this would essentially improve the economy of the overall process.

Ethanol is a well-known compound which has a wide use. Ethanol has attracted interest as an alternative liquid fuel. If the ethanol production process only uses energy from renewable energy sources, no net carbon dioxide is added to the atmosphere, making ethanol an environmentally beneficial energy source.

It is known that ethanol can be produced from cellulose and hemicellulose by fermenting with a suitable yeast strain. The production of ethanol from D-xylose has been described in U.S. Pat. No. 4,368,268 (C-S. Gong), which is directed to the manufacturing of mutants that produce ethanol in high yields, and in *Biotechnology* and *Bioengineering Symp.* 12 (1982), pp. 91102, McCracken, L. & Gong, C-S., which is directed to fermentation with thermotolerant yeasts.

Ethanol production from lignocellulosic material can comprise the following steps: (1) degradation of the lignocellulosic structure to a fermentable substrate, (2) fermentation of the fermentable substrate, and (3) distillation of the fermentation broth to obtain ethanol.

In the past, there have been problems encountered in the efficient conversion of the lignocellulosic hydrolysates to ethanol. First, after pretreatment, the hydrolysate contains not only fermentable sugars, but also a broad range of compounds which often have inhibitory effects in the microorganisms used for fermentation. The composition of these compounds depends upon the type of lignocellulosic material used and the chemistry and nature of the pretreatment process. Second, the hemicellulose hydrolysates contain not only hexoses but also pentoses. The pentose fraction in hemicellulose comprises mainly xylose, but depending on the raw material origin, the arabinose fraction may be substantial. While some hexoses can readily be fermented, pentoses are more difficult to ferment.

Lignocellulosic materials are composed of mainly cellulose, hemicellulose, and lignin. Cellulose is a linear, crystalline polymer of $\beta$-D-glucose units. The structure is rigid and harsh treatment is usually required to break down cellulose. Hemicellulose has usually as a main component linear and branched heteropolymers of L-arabinose, D-galactose, D-glucose, D-mannose, D-xylose and L-rhamnose. The composition of hemicelluose varies with the origin of the lignocellulosic material. The structure is not at least totally crystalline and is therefore usually easier to hydrolyze than cellulose. Examples of lignocellulosic materials considered for ethanol production are hardwood, softwood, forestry residues, agricultural residues, and municipal solid waste (MSW). Both cellulose and hemicellulose can be used for ethanol production. The pentose content in the raw material is of importance as pentoses are often difficult to ferment to ethanol. The pentose content can comprise 6-28% of the total dry matter. To achieve maximum ethanol yield, all monosaccharides should be fermented. Softwood hemicellulose contains a high proportion of mannose and more galactose and glucose than hardwood hemicellulose whereas hardwood hemicellulose usually contains a higher proportion of pentoses like D-xylose and L-arabinose.

The degradation of the lignocellulosic structure often requires many steps. The first step can comprise prehydrolysis in which the hemicellulose structure is broken down. The second step can comprise the hydrolysis of the cellulose fraction in which lignin will remain as a solid by-product. The two hydrolyzed streams can be fermented to ethanol either together or separately, whereafter they can be mixed together and distilled.

As previously discussed, during the degradation of the lignocellulosic structure, not only fermentable sugars are released, but a broad range of compounds, some of which can inhibit the effectiveness of the microorganism used for fermenting. The amount and nature of inhibiting compounds depends on the raw material, the prehydrolysis and hydrolysis procedures, and the extent of recirculation in the process. Fermentation inhibitors in lignocellulosic hydrolysates can be divided into several groups depending on their origin. Substances released during prehydrolysis and hydrolysis include acetic acid, which is released when the hemicellulose structure is degraded and extractives. The extractives can comprise terpenes, alcohols, and aromatic compounds such as tannins. The inhibitory effect of acetic acid is pH dependent. The fermentability of a lignocellulosic hydrolysate can be improved by raising the pH. Furthermore, a group of inhibitors, such as furfural, 5-hydroxymethyl furfural, laevulinic acid, formic acid, and humic substances are often produced as by-products in prehydrolysis and hydrolysis due to the degradation of sugars. Moreover, lignin degradation products are often produced in prehydrolysis and hydrolysis. This group of inhibitors includes a wide range of aromatic and polyaromatic compounds with a variety of substituents. Also, products of the fermentation process, such as ethanol, acetic acid, glycerol, and lactic acid, inhibit the microorganism. The influence of these compounds will be especially evident in recirculation systems. Furthermore, metals released from the equipment and additive such as sulfur dioxide ($SO_2$) can also inhibit fermentation.

It is, therefore, desirable to provide an improved method to produce ethanol, as well as perhaps other important products, such as xylitol, from lignocellulose-containing material in biomass.

BRIEF SUMMARY OF THE INVENTION

An improved method is provided to produce ethanol, as well as perhaps other important products, such as xylitol, from lignocellulose-containing material in biomass. Advantageously, the method is effective, economical and attractive.

In the method, lignocellulose-containing material from xylan-containing matter in biomass comprising pentose and hexose, is processed by hydrolysis or partial hydrolysis to produce a processed solution comprising free pentoses and hexoses. The processed solution can be fermented with microbes to produce a fermented solution comprising fermented ethanol and spent microbes. During fermenting, a substantial amount of hexose in the processed solution is converted to ethanol. Fermented liquid derived from the fermented solution can be distilled to produce distilled ethanol. Advantageously, the distilled ethanol comprises a greater concentration of ethanol by weight on a liquid basis than the ethanol in the fermented solution.

The lignocellulose-containing material can comprise at least one lignocellulosic material, such as cellulose, hemicellulose, or lignin. The xylan-containing matter can comprise one or more of the following: wood, softwood as pine and spruce hardwood as alder, aspen, birch, beech, eucalyptus, maple, poplar, willow, plants as plant constituents, grain as wheat, barley, rice, rye and oat, particulates of grain as straw, hulls, husks, fiber, shells, stems, corn cobs, corn straw, corn fiber, nutshells, almond shells, coconut shells, bagasse, cotton seed bran, cotton seed skins, wood chips, sawdust, woodpulp, processed paper, spent sulphite liquor, spent liquor from paper processing, spent liquor from woodpulp processing, sulphite cooking liquor, or liquids derived from any of the preceding.

The processed solution can comprise biomass hydrolysates. The biomass hydrolysates can be obtained by: direct acid hydrolysis of the biomass, enzymatic prehydrolysate obtained by prehydrolysis of the biomass with steam or acetic acid, acid hydrolysis of prehydrolysate obtained by prehydrolysis of the biomass with steam or acetic acid, or a sulphite pulping process. The biomass hydrolysates can also comprise or be derived from: spent sulphite pulping liquor, acid spent sulphite liquor, spent liquor from softwood pulping before hexoses are removed, spent liquor from softwood pulping after hexoses are removed, spent liquor from hardwood pulping, spent liquor from digestion of the biomass, spent liquor from hydrolysis of the biomass, spent liquor from solvent-based pulping, spent liquor from thanol-based pulping, spent liquor from sulphate-prehydrolysis pulping, mother liquor from crystallization of xylose, and diluted runoff of xylose crystallization of sulphite spent pulping liquor derived solution.

The pentose can comprise at least one pentose-containing material, such as D-xylose or L-arabinose. During fermentation, L-arabinose in the processed solution can be reduced (converted) to arabinitol. The hexose can comprise at least one hexose-containing material, such as: D-glucose, D-galactose, L-rhamnose, D-mannose, or other monosaccharides.

The fermented solution can also comprise xylitol and fermenting can also comprise reducing (converting) xylose in the processed solution to fermented xylitol. The fermented xylitol can be treated to remove ethanol by distillation and xylitol will remain as a bottom product (distilled xylitol). The xylitol as a bottom product can comprise a greater concentration of distilled xylitol by weight on dry substance (solids) basis than the fermented xylitol in the fermented solution.

The xylitol bottom product can also be separated to produce a xylitol product and residue. The xylitol product can comprise a greater concentration of xylitol by weight on a dry substance (solids) basis than the distilled xylitol in the xylitol bottom product. Separation of the xylitol bottom product can be accomplished by chromatographic separation, such as by: batch separation, continuous simulated moving bed separation, or sequential simulated moving bed separation. Separation of the xylitol bottom product can also be accomplished by filtering, such as by: membrane filtration, ultrafiltration, nanofiltration, or microfiltration. The filtering can also comprise passing the xylitol bottom product through at least one membrane, such as: a high shear membrane, a vibrating membrane, a rotating membrane, a flat sheet membrane, a tubular membrane, a spiral membrane, a hollow fiber membrane, a neutral charged membrane, an ionic membrane, a cationic membrane, or an anionic membrane.

Xylitol and xylitol product can be recovered either as a liquid xylitol or crystallized to produce xylitol crystals. Crystallization can be accomplished by different methods, e.g. by cooling crystallization The xylitol crystals can be separated by centrifugation or filtration and optionally washed with water to produce substantially pure crystalline xylitol.

The method can further include removing solids from the processed solution. Furthermore, the method can include:

separating a substantial portion of the spent microbes from the fermented solution prior to or after distillation to produce fermented liquid derived from the fermented solution. The fermented liquid can comprise ethanol, as well as substantially less spent microbes by weight on a dry substance (solids) basis than the spent microbes in the fermented solution. A substantial portion of the spent microbes can be separated from the fermented solution by filtration, centrifugation, and decanting.

Processing of the lignocellulose-containing material can further comprise at least one of the following: prehydrolysis of the lignocellulose-containing material, steam explosion of the lignocellulose-containing material, enzymatic hydrolysis of the lignocellulose-containing material with enzymes having a cellulolytic and hemicellulolytic e.g. xylanolytic activity to hydrolyze the lignocellulose-containing material, acid hydrolysis of the lignocellulose-containing material, chromatographic separation, ion-exchange purification, precipitation, partial hydrolysis of the lignocellulose-containing material, or extraction of the lignocellulose-containing material.

The prehydrolysis process can be performed by physical, chemical, or biological methods such as steam pretreatment, milling, steam explosion, acid treatment (e.g. hydrochloric acid, phosphoric acid, sulfuric acid, sulfur dioxide), alkaline treatment (e.g. sodium hydroxide, ammonia), or treatment with organic solvents (e.g. ethanol, ethylene glycol) or white rot fungi. In the prehydrolysis step, the hemicellulose can be liquefied which can sometimes result in a mixture of monosaccharides and oligosaccharides.

The hydrolysis of the cellulose can be performed by weak acids or by enzymes. Concentrated hydrochloric acid or sulphuric acid can also be utilized. If desired, the prehydrolysis and hydrolysis can be carried out in one step or two. Generally, acid hydrolysis procedures give rise to a broad range of compounds in the resulting hydrolysate, some of which might negatively influence the subsequent steps in the process. A strong and weak acid hydrolysis process can be combined with a weak acid prehydrolysis or alkaline treatment.

Processing can further comprise partially hydrolyzing the lignocellulose-containing material. The partially hydrolyzed lignocellulose-containing material can be separated into an extracted biomass comprising hexosans as glucans and a prehydrolyzate comprising free hexoses and pentoses as xylose. The extracted biomass can be hydrolyzed to produce a hydrolyzate comprising hexoses. Fermenting can further comprise: fermenting the hydrolyzate to produce a fermented solution comprising ethanol; and fermenting the prehydrolyzate to produce a fermented solution comprising xylitol.

The method can further comprise post processing the processed solution in at least one post processing step, such as: crystallization, chromatography, ion-exchange, concentration, evaporation, reverse osmosis, color removal e.g. by carbon or resin, reduction, detoxification, or catalytic hydrogenation. Furthermore, the processed solution can be detoxified to help remove inhibitors prior to fermenting by one or more of the following: overliming, calcium hydroxide addition, hydroxide addition, pH adjustment, concentration e.g. by evaporation, filtering, activated charcoal treatment, extraction with organic solvents, ion exchange, ion exclusion, molecular sieves, steam stripping, heating, removing furfural, stripping volatile compounds, and reducing of the processed solution by sulphite addition.

The microbes used to ferment the processed solution can comprise at least one fermenting microorganism, such as: naturally occurring bacteria, recombinant bacteria, naturally occurring yeast, recombinant yeast, or fungi. The naturally occurring bacteria can comprise: *Bacillus macerans* DMS 1574, *Bacteroides polypragmatus* NRCC 2288, *Clostridium saccharolyticum* ATCC 35040, *C. thermohydrosulfurcium* 39E, *C. thermohydrosulfurcium* ATCC 31925,*Erwinia chrysanthemi* 8374, *Thermoanaevobacter ethanolicus* ATTC 31938, *Lactobacillus brevis*, or *Lacococcus lactis ssp. Lactis*. The recombinant bacteria can comprise: *Erwinia chrysanthemi* 8374, *Escherichia coli* B, *E. coli* B KO11, *Koebsiella oxytoca* M5A1, *K. planticola* SDF20, *Zymomonas mobilis* CP4, or *Z. mobilis* NRRL 14023.

The naturally occurring yeast can comprise: *Candida blanki* ATCC 18736, *C. acidothermophilum* ATCC 20831, *C. brassicae* ATCC 32196, *C. famata*, *C. fructus* JCM 1513, *C. guilliermondii* ATCC 22017, *C. shehatae* CBS 4705, *C. shehatae* CSIR Y492, (also CBS 2779 and ATCC 60778), *C. shehatae* ATCC 22984 sp CSIR 62 A/2, *C. tenius* CBS 4435, *C. tropicalis* KY 5014, *C. tropicalis* ATCC 20240, *C. tropicalis* ATCC 9968, *C. tropicalis* NRRL y 11860, *Clavispora* sp. UWO 83-833-1, *Kluyveromyces cellobiovous* KV 5199, *K. marxianus, Pachysolen tannophilus* NRRL Y 2460 (also ATCC 32691), *P. tannophilus* RL 171, *Pichia segobiensis* CBS 6857, *P. stipitis* CBS 5773, *P. stipitis* CBS 5776, *P. stipitis* NRRL Y 1714, *Schizosaccharomyces pombe* ATCC 2478, *Hansenula anomala* ATCC 34080, *Kluyveromyces fragilitis* ATCC 12424, *Saccharomyces uvarum* ATCC 24556, *S. uvarum* ATCC 26602, *F. oxysporum*, or *Debaryomyces hansenii*.

The recombinant yeast can comprise *Saaccharomyces cerevisiae*, *S. cerevisiae* TJ1, *S. cerevisiae* H550, *S. cerevisiae* ATCC 24860, *Schizosaccharomyces pombe* ATCC 2456, or *S. pombe* NRRL Y164.

The filamentous fungi can comprise: *Aeurobasidium pullulans, Fusarium avenaceium* VTT-D-80146, *F. clamydosporum* VTT-D-77055, *F. culmorum* VTT-D-80148, *F. graminearurn* VTT-D-79 129, *F. lycopersici* ATCC 1541 7, *F. oxysporum* VTT-D-80 134, *F. sembucium* VTT-D-77056, *F. solani* VTT-D-80139, *Monilia* sp., *Mucor* sp. 105, *Neurospora crassa* NCIM 870, or *Paecilomyces* sp. NFI ATCC 20766.

Preferably, the fermenting microorganism is a yeast of the genera *Candida, Pichia, Pachysolen,* or *Debaryomyces*, such as: *Candida tropicalis, Candida tropicalis* strain having accession number ATCC 9968, which is available from The American Type Culture Collection (ATCC), 10801 University Boulevard, Manassas (Va.), 20110-2209, U.S.A, *Pachysolen tannophilus* NRRL Y-2460, which is available from the Microbial Genomics and Bioprocessing Research Unit, National Center for Agricultural Utilization Research, 1815 N. University Street, Peoria, Ill. 61604, U.S.A. and is also available from the ATCC under ATCC accession number 32691, *Candida shehatae* CBS 2779, which is available from The Centraalbureau voor Schimmelcultures (CBS)—an institute of the Royal Netherlands Academy of Arts and Sciences, Uppsalalaan 8, 3584 CT Utrecht, The Netherlands, whose postal address is P.O. Box 85167, 3508 AD Utrecht, The Netherlands and is also available from the ATCC under ATCC accession number 60778, *Pachysolen tannophilus* NRRL Y-2460, the ATCC under accession number 32691 or *Debaryomyces hansenii* ATCC 10620, which is available from the ATCC.

Fermenting can occur as continuous or batch fermentation at a temperature ranging from about 10 to about 45 degrees C. at a pH ranging from 4 to 7 with a yeast concentration of about 1 to about 40 g of dry yeast per liter of processed solution for about 24 to about 96 hours in the presence of at least one nutrient. The nutrient can comprise: a yeast extract, diammoniumphosphate, peptone, biotin, thiamin, folic acid, a water soluble vitamin, a fat soluble vitamin, vitamin A, vitamin B complex, vitamin D, vitamin E, vitamin K, vitamin B 1, vitamin B2, vitamin B5, vitamin B6, vitamin B12, vitamin B15, or another vitamin.

A more detailed explanation of the invention is provided in the following description and appended claims taken in conjunction with the accompanying drawings.

DETAILED DESCRIPTION OF THE INVENTION

Figure 1:
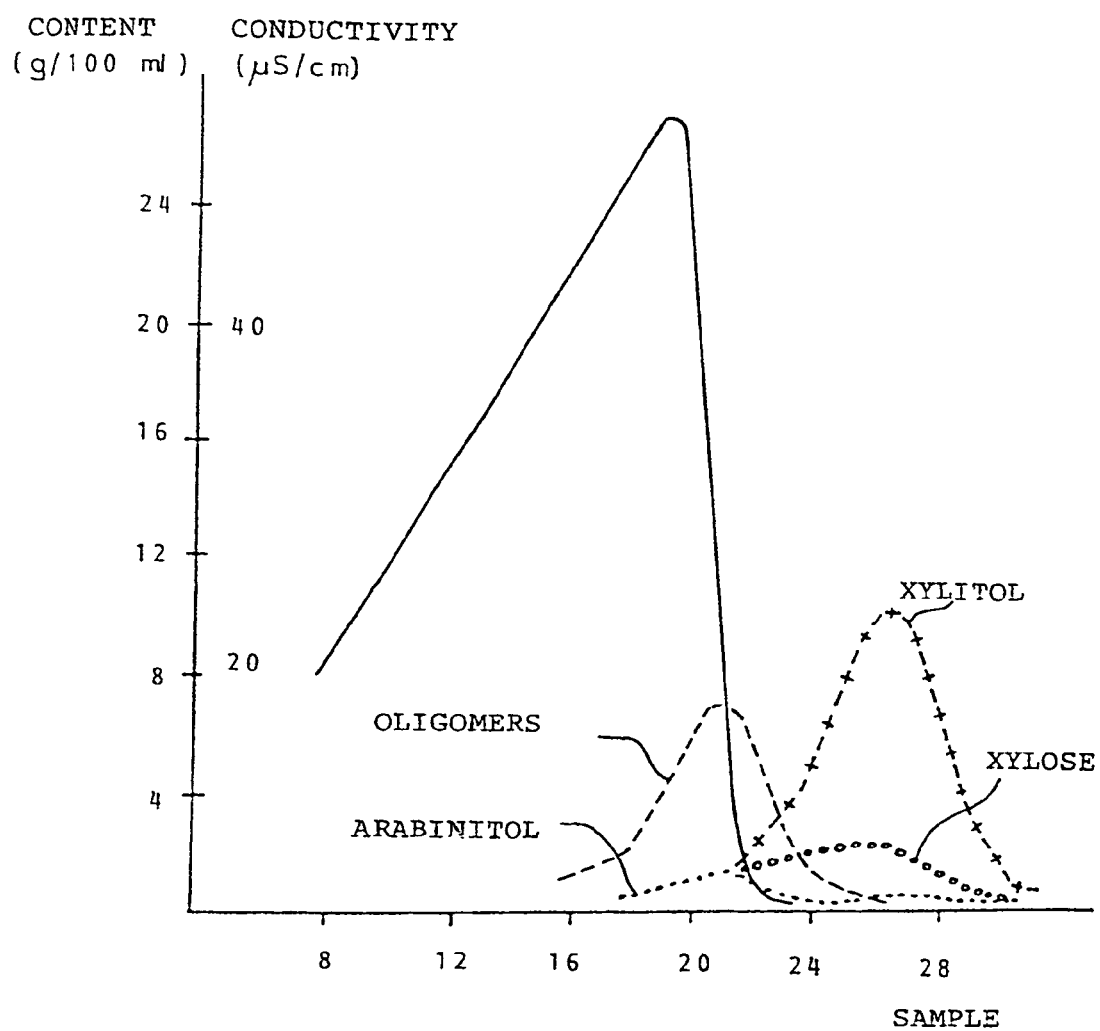
FIG. 1 illustrates a graph of chromatographic separation.

The following is a detailed description and explanation of the preferred embodiments of the methods of the invention along with some examples thereof.

It has now been found that xylitol and ethanol can be produced and recovered simultaneously by one of the processes of the invention wherein xylose is mainly converted to xylitol but alternatively converted into ethanol while the majority of the hexoses present in the raw material are converted to ethanol. Thus the raw material is effectively utilized and at least two commercially very important products are obtained in a pure form and with a high yield. The process is beneficial and effective.

The process of the invention can be characterized in that the hydrolyzed starting material is fermented with a microbe e.g. yeast strain, the ethanol produced is recovered, a separation is carried out on the remaining xylitol solution, and pure xylitol may be crystallized. Xylose-containing substances can be used as starting materials and can be fermented with a yeast strain or other microbes that are capable of converting xylose to xylitol and/or ethanol and most hexoses to ethanol. By fermentation, a xylitol-rich solution is obtained wherefrom xylitol is recovered. Generally the xylitol can be purified, such as by chromatographically, membraneseparation, etc., whereafter it can be crystallized to obtain pure xylitol. Ethanol can be removed from the fermentation solution such as by distillation. Therefore, the need for separating xylitol from the hexitols and other sugars produced in the hydrolysis and reduction steps can be avoided to great extent. Advantageously, the hydrolysis performed in accordance with the invention also provides a solution to the problem of using pulp discarded as waste mass in other processes, and thus in the process of the invention substantially the entire starting material is utilized.

Almost any xylan-containing material can be used as a starting material in the process of the invention. Possible starting materials include wood, softwood as pine and spruce, hardwood such as alder, aspen, birch, beech, maple, poplar, eucalyptus, willow etc., and plants or plant constituents, grains as wheat, barley, rice, rye and oat, particulates of grain as straw, hulls, husks, fiber, shells, stems corn cobs, corn straw, corn fiber, nutshells, almond shells, coconut shells, bagasse, and cottonseed bran, cottonseed skins. When wood is used as a starting material, it is advantageously comminuted or used as chips, sawdust, etc. and treated by hydrolysis or steam explosion and posthydrolysis, in which connection a carbohydrate material useful in this invention is obtained.

In addition to the above, for instance by-products which are formed in processing. and production of woodpulp and which have a high xylan or xylose content can be used. As an example may be mentioned the acid sulphite spent liquor produced in the manufacture of woodpulp by the sulphite pulping process, said spent liquor containing small quantities of undissolved wood solids, and soluble substances such as lignosulphonates, hexoses and pentoses, including xylose, and being a good raw material for use in the production of xylitol. Other by-products and spent products produced in the processing of paper and woodpulp, such as prehydrolysates from the production of dissolving pulp and spent liquor from the so called neutral sulphite pulping process, which have a high xylan and/or xylose content, can also be used.

The process of the invention can employ an aqueous solution containing free xylose. Thus it may be necessary to carry out an acid and/or enzyme hydrolysis on the starting material to break down the xylan into xylose. Processes for hydrolyzing xylan-containing materials to produce xylose-containing solutions have been described e.g. in U.S. Pat. No. 3,784,408 (Jaffe et al.) and U.S. Pat. No. 3,586,537 (Steiner et al.).

The starting material may, if desired, be pretreated before the fermentation to remove constituents which may be toxic or otherwise disadvantageous to the yeast or other microbes. The necessity of the pretreatment step is dependent on the starting material used and the yeast or other microbes used in the fermentation step. The pretreatment of the starting material may include for instance posthydrolysis, chromatographic separation, ion exchange purification, precipitation, steam stripping etc.

Figure 2:
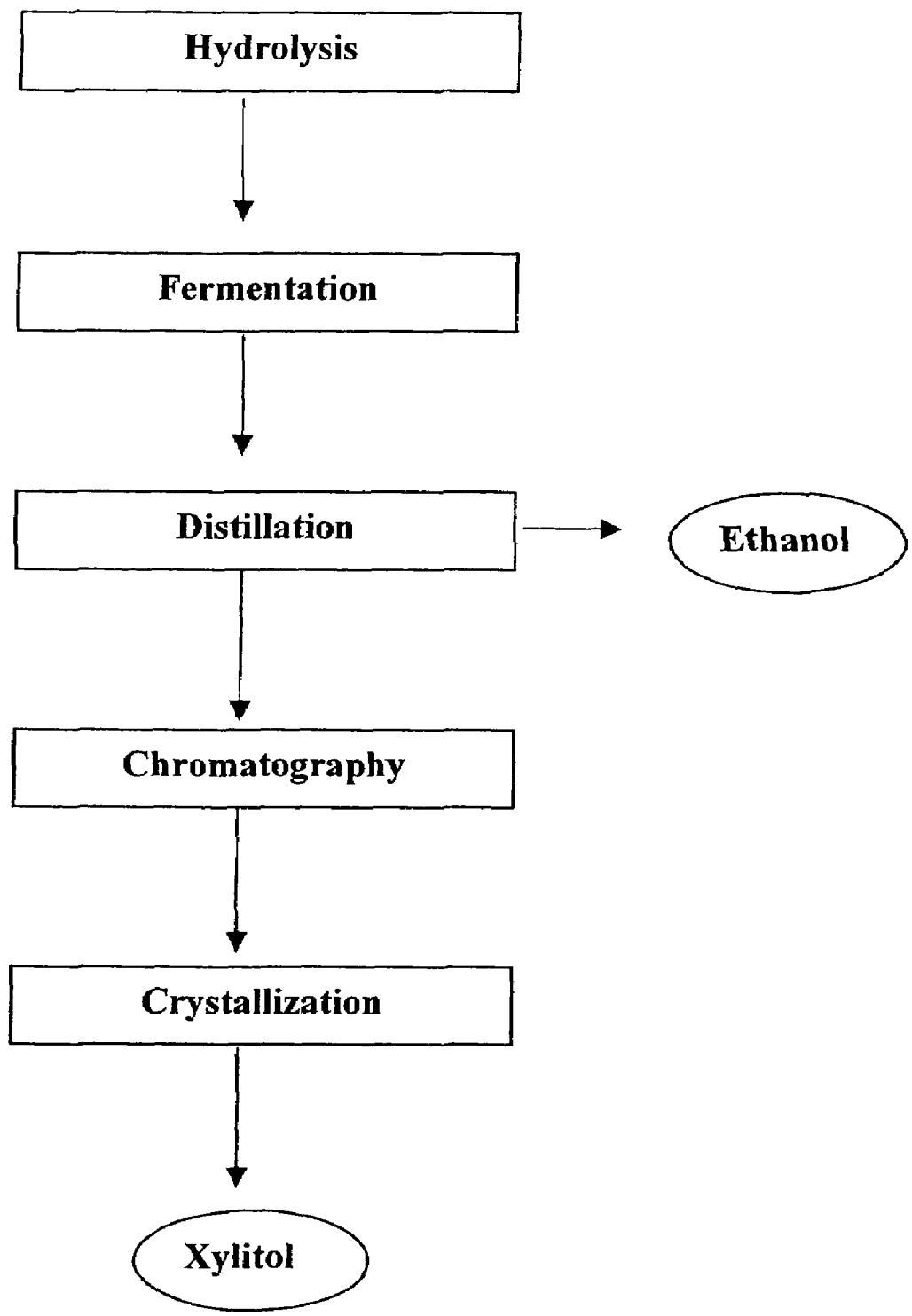
FIG. 2 illustrates a process flow chart of one method of the invention.
Figure 3:
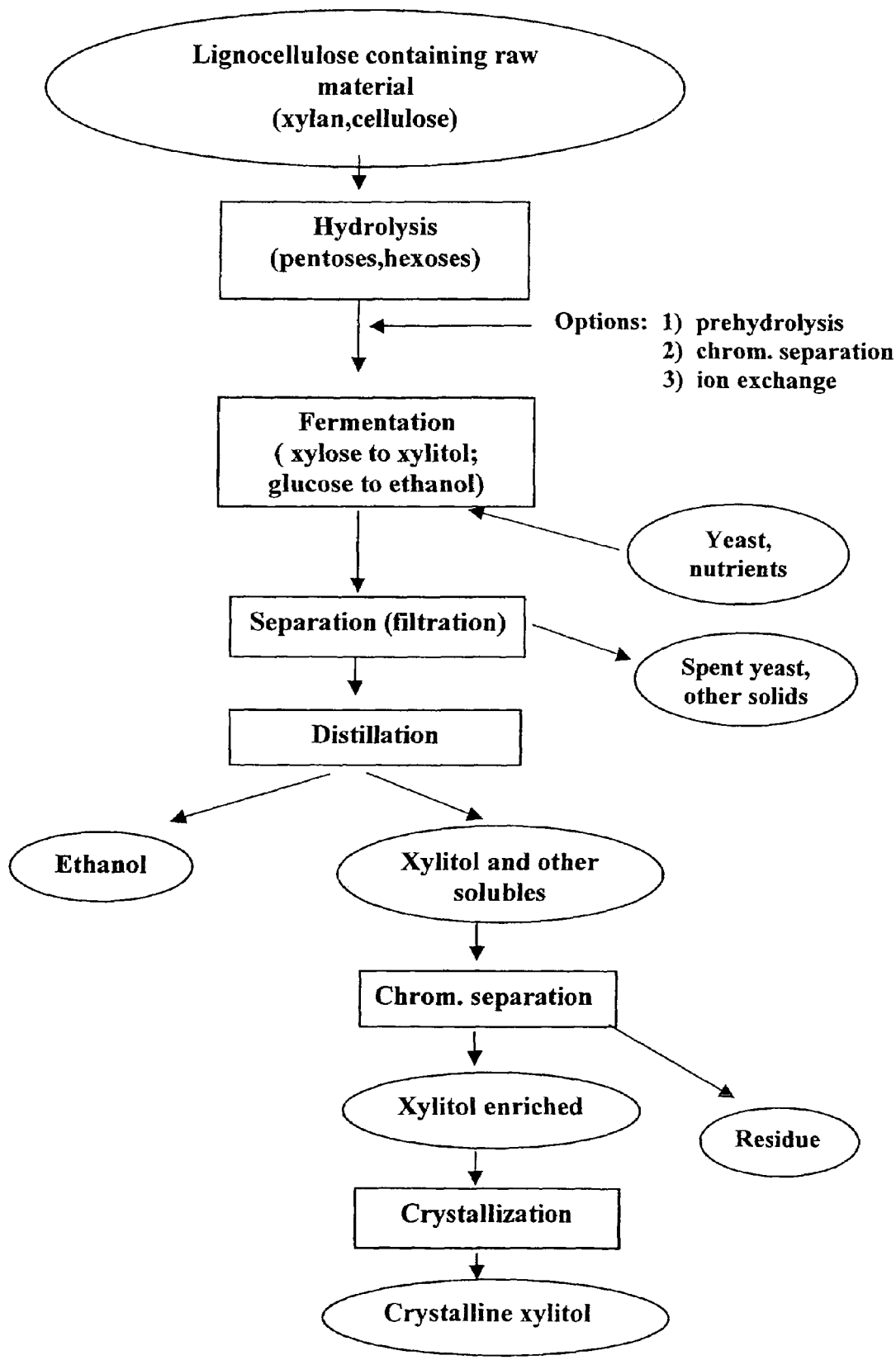
FIG. 3 illustrates a process flow chart of another method of the invention.
Figure 4:
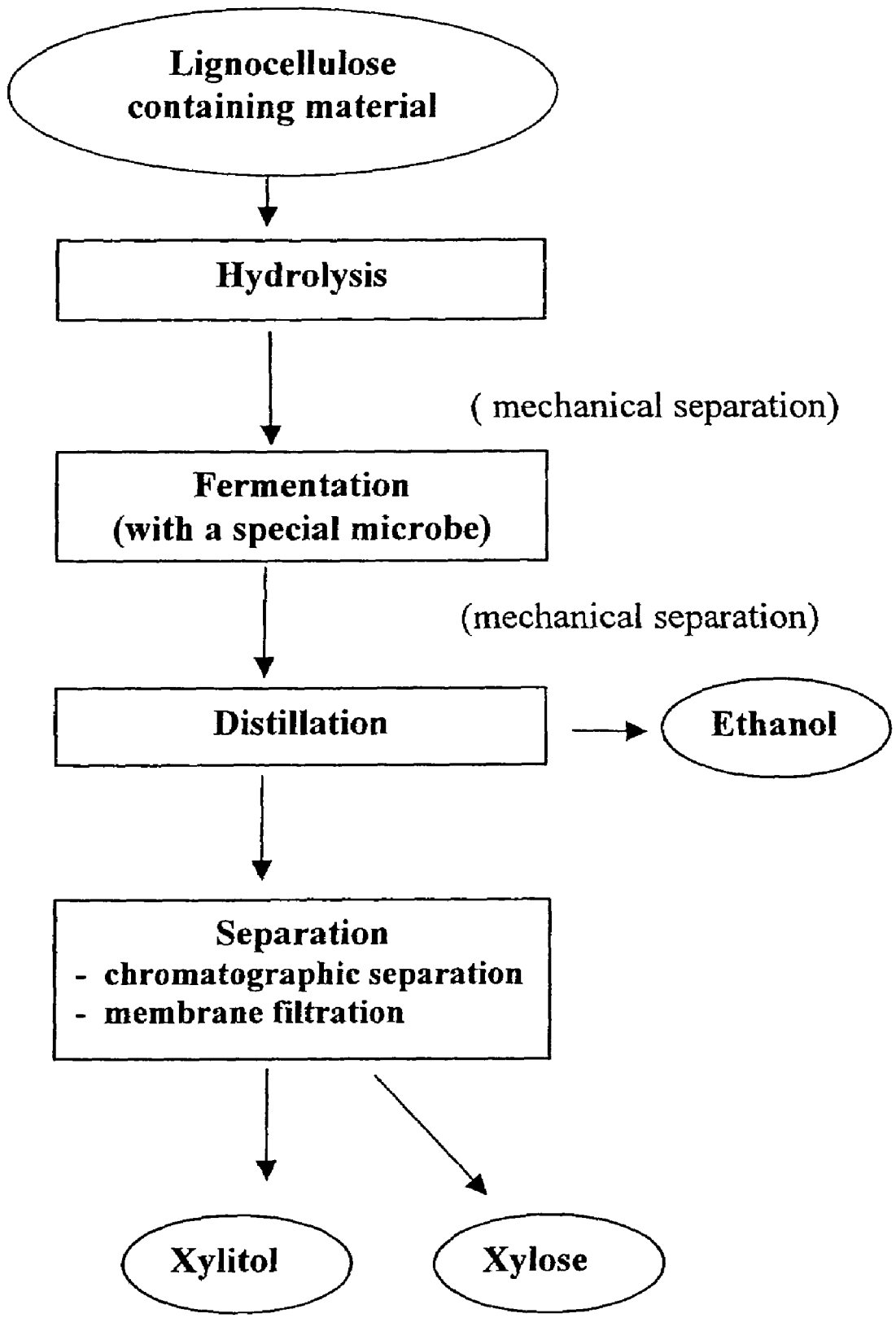
FIG. 4 illustrates a process flow chart of a further method of the invention.
Figure 5:
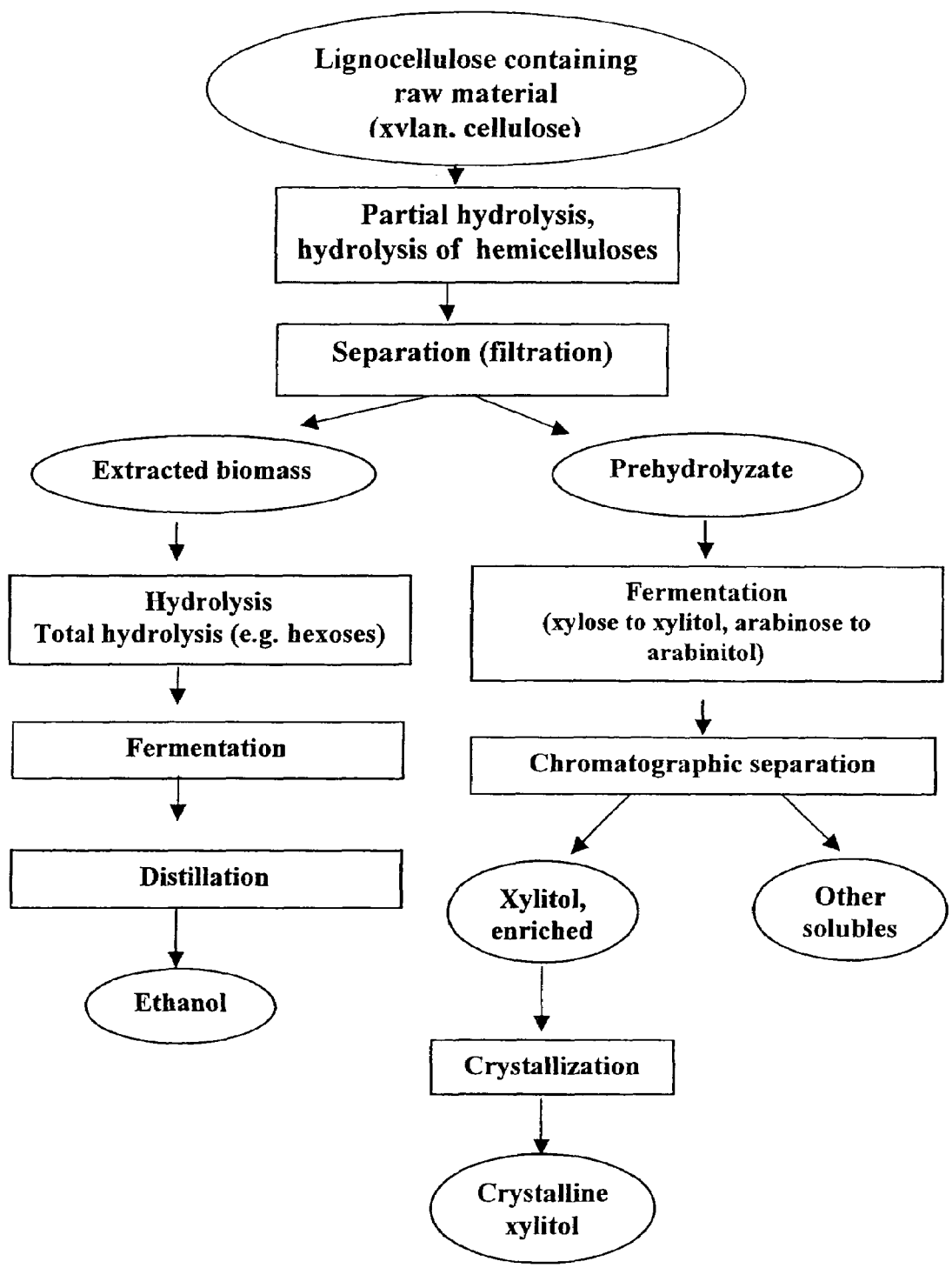
FIG. 5 illustrates a process flow chart of still another method of the invention.
Figure 6:
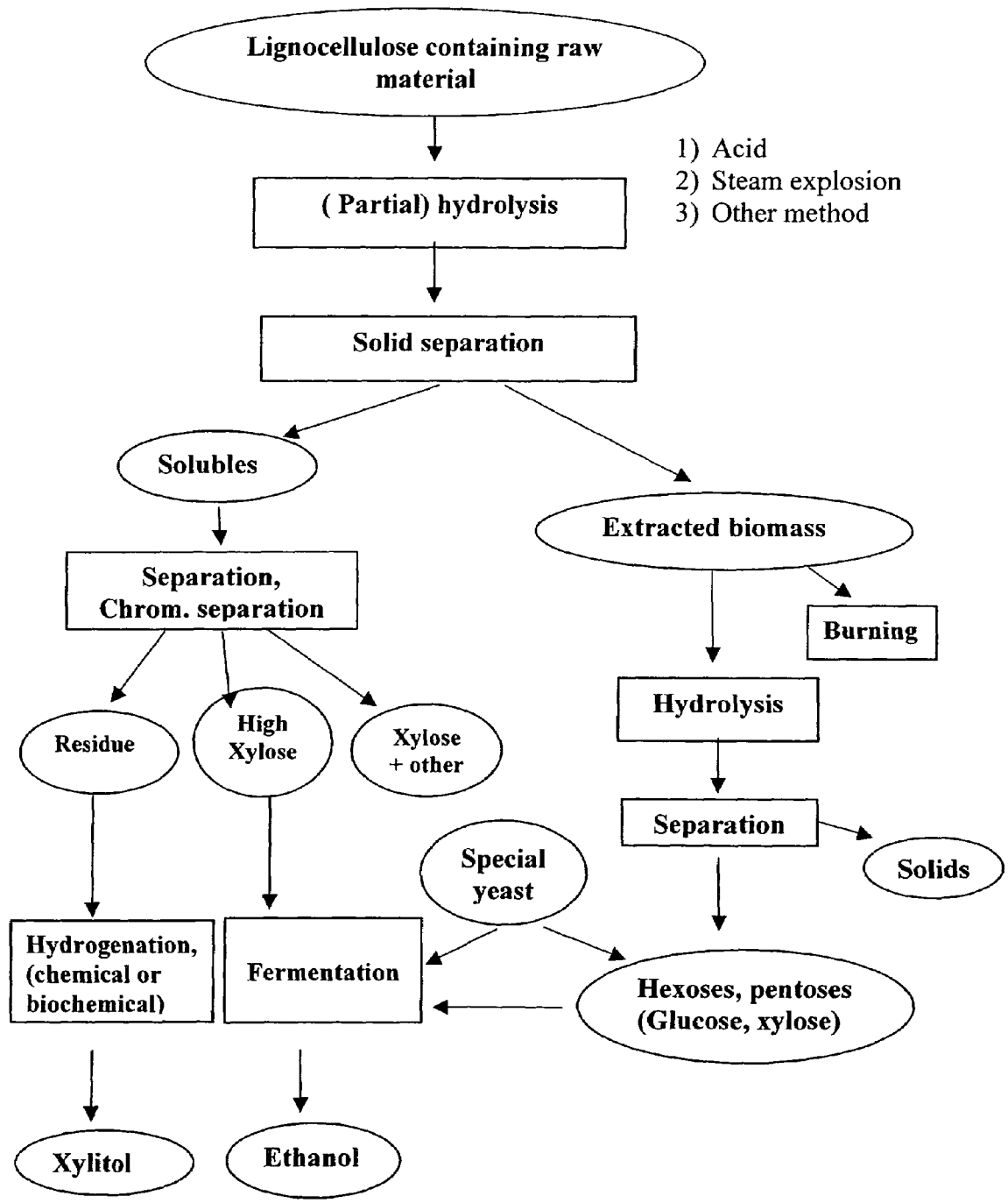
FIG. 6 illustrates a process flow chart of still a further method of the invention.

One method of the invention is illustrated in the process flow chart of FIG. 2.

The hydrolysis can comprise two steps, prehydrolysis of the cellulose-containing raw material, which may be effected using the so called steam explosion method, weak acid hydrolysis and the enzymatic hydrolysis of the polysaccharides and oligosaccharides to produce the corresponding monosaccharides. This step can be carried out using enzymes which have a high cellulolytic and xylanolytic activity.

The remaining solids, consisting for the most part of lignin and cellulose, can be then separated from the solution obtained. Alternatively, the solids and the solids produced in the fermentation, such as spent yeast or other spent microbes, can be separated or collected before or after the next distillation.

When relatively impure solutions are used as a starting material, pretreatment of the solutions may be necessary in some cases. The pretreatment may be e.g. posthydrolysis and/or separation of the constituents which may be toxic and/or disadvantageous to the yeast employed or which have an adverse effect on the fermentation or separation steps. The pretreatment may also be combined with chromatographic separation, ion exchange purification, precipitation, etc.

Thereafter, the solution can be fermented with a suitable yeast strain or other microbes. One embodiment of the invention employs yeasts that are capable of reducing xylose into xylitol and hexoses into ethanol and/or use hexoses for their growth. Such yeasts are for instance yeasts of the genera *Candida, Pichia, Pachysolen,* mutated *Saccharomyces, Debaryomyces. Candida* and *Debaryomyces* species, particularly *Candida tropicalis* and *Debaryomyces hansenii,* are regarded as advantageous. As a good example may be mentioned the *Candida tropicalis* strain deposited at the American Type Culture Collection under the accession number ATCC 9968. The xylose content of the aqueous solution to be fermented is dependent on the starting material and process steps employed, but is advantageously about 50-300 g/l.

The fermentation can be carried out in most commercially available fermentors which are furnished with aerating means and stirring and pH regulating means. The temperature is advantageously about 20-40 degrees C, most advantageously about 30 degrees C. The yeast cells are added to the xylose-rich solution. Generally, it can be said that the higher the yeast concentration, the faster the fermentation step is. It has been found that the yeast concentration is advantageously about 1-20 g (up to 30-50 g) of dry yeast/i of substrate (dry weight) when the xylose content is about 50-300 g/l.

The fermentation can be enhanced by adding nutrients, as in one batch, until the most part of the xylose has been converted to xylitol and substantially all hexoses have been converted to ethanol and/or used for yeast growth. The fermentation generally takes about 24-144 hours, preferably 24-72 hours. With the process of the invention, up to 90% of the xylose can be converted to xylitol and part to ethanol.

After the fermentation step, the solution can be clarified prior to the separation of xylitol and ethanol therefrom. The spent yeast cells or other spent microbes can be removed after the fermentation. This may be carried out by centrifugation, filtration, decanting or some other procedure. When the spent yeast cells or other spent microbes have been removed and the solution is clear, the ethanol produced in the fermentation can be recovered by evaporation, distillation or some other procedure. Alternatively, the removal of the spent yeast cells or other spent microbes can be carried out after the distillation.

To recover xylitol, chromatographic separation can be first performed. This is advantageously carried out in a column filled with a sulphonated polystyrene resin cross-linked with divinylbenzene in the alkaline-earth or alkali metal form. A large-scale chromatographic method suitable for this purpose has been described in U.S. Pat. No. 3,928,193 (Melaja et al.). The chromatographic separation can also be carried out using a simulated moving bed, such as described in U.S. Pat. No. 2,985,589.

From the fraction having a high xylitol content obtained from the chromatographic step or after additional purification, xylitol can be crystallized with a good yield using conventional crystallization methods, such as cooling crystallization. When cooling crystallization is used, xylitol crystals of an average diameter of about 30 μm are added as seed crystals to the concentrated xylitol solution, whereafter the temperature of the solution can be slowly decreased. The crystals obtained, the average diameter of which is about 250-600 μm, can be separated for instance by centrifugation or filtration and washed with water to obtain substantially pure crystalline xylitol.

The process can also be carried out in a preferable alternative way so that the starting material is subjected to partial hydrolysis and extraction. The prehydrolysate obtained from the extraction can then fermented to convert xylose to xylitol, which can be separated chromatographically and crystallized in the above-stated manner. A final hydrolysis can be carried out on the extracted mass, the hydrolysis product can be fermented to convert hexoses to ethanol, and ethanol can be recovered in the manner described above or using other methods as membrane process, pervaporation or reverse osmosis.

Other methods of the invention are illustrated in the process flow charts of FIGS. 3-6 and/or are described in the specification of this application.

In one method, lignocellulose-containing material from xylan-containing matter in biomass comprising pentoses and hexoses is hydrolyzed to produce a hydrolyzed solution comprising free pentoses and hexoses. The hydrolyzed solution can be fermented with microbes to produce a fermented solution comprising fermented ethanol, fermented xylitol-producing solution, fermented xylose, and spent microbes. During fermentation a substantial amount of the hexose in the hydrolyzed solution can be converted to fermented ethanol. Also, during fermentation a substantial amount of the pentose in the hydrolyzed solution can be reduced to fermented xylitol solution, fermented xylose and fermented ethanol.

Fermented liquid derived from the fermented solution can be distilled to produce distilled ethanol and a distilled solution comprising distilled xylitol solution, distilled xylose and spent microbes. The distilled ethanol can comprise a greater concentration of ethanol by weight on a liquid basis than the fermented ethanol in the fermented solution. The bottom product can also have a greater concentration of distilled xylitol-producing solution by weight on a dry substance (solids) basis than the fermented xylitol-producing solution in the fermented solution.

The bottom product can be separated by fractionating the distilled solution into fractions comprising a separated xylitol-producing fraction and a separated xylose fraction. The separated xylitol-producing fraction can comprise a greater concentration of xylitol-producing solution by weight on a dry substance (solids) basis than the distilled xylitol-producing solution in the distilled solution.

The hydrolyzed solution can be post treated by one or more of the following: pH adjustment, concentration, filtration, filtering with a pressure filter, filtering with diatomaceous earth, chromatographic separation, detoxification, removing inhibitors, liming, calcium hydroxide addition, calcium oxide addition, sodium hydroxide addition, activated charcoal treatment, extraction with organic solvents, ion exchange, ion exclusion, treatment with molecular sieves, steam stripping, heating, removing furfural, stripping volatile compounds, and reduction of the hydrolyzed solution by sulphite addition. Advantageously, the xylitol-producing solution has a greater concentration of at least one compound, such as xylitol, xylose, arabinose, mannose, or galactose and rhamnose, on a dry substance (solids) basis than the compound in the hydrolyzed solution.

The distilled solution can be-separated by chromatographic separation, such as by: batch separation, continuous simulated moving bed separation, or sequential simulated moving bed separation. The distilled solution can also be separated by filtering, such as by: membrane filtration, ultrafiltration, nanofiltration, or microfiltration. The filtering can comprise passing the xylitol bottom product through at least one membrane, such as: a high shear membrane, a vibrating membrane, a rotating membrane, a flat sheet membrane, a tubular membrane, a spiral membrane, a hollow fiber membrane, a neutral charged membrane, an ionic membrane, a cationic membrane, or an anionic membrane.

The process can further include: hydrogenating the xylitol-producing fraction to produce hydrogenated xylitol, and/or hydrogenating of the separated xylose fraction to produce hydrogenated xylitol.

The xylitol fraction and/or hydrogenated xylitol can be crystallized to produce xylitol crystals. Crystallization can be accomplished by different methods, such as: cooling crystallization or evaporation crystallization or both or combination. The xylitol crystals can be separated e.g. by centrifugation and filtration and optionally washed with water to produce substantially pure crystalline xylitol.

The method can also include separating a substantial portion of the spent microbes from the fermented solution prior to the distilling to produce fermented liquid derived from the fermented solution. Such separation (clarification) can be accomplished by: filtration, centrifugation, flocculation, flotation and decanting. The fermented liquid can comprise: fermented ethanol, fermented xylitol, fermented xylose, and spent microbes. The fermented liquid can desirably comprise substantially less spent microbes by weight on a dry substance (solids) basis that the spent microbes in the fermented solution. A substantial amount of solids from the hydrolyzed solution can further be removed before fermenting, by at least one removal step, such as by: filtration, centrifugation, decanting and clarification using flocculation.

Hydrolyzing of the lignocellulose-containing material can be accomplished by enzymatic hydrolysis of the lignocellulose-containing material with enzymes having a cellulolytic and xylanolytic activity to hydrolyze the lignocellulose-containing material, or by acid hydrolysis of the lignocellulose-containing material.

The lignocellulose-containing material can also be pretreated before hydrolyzing. Such pretreatment can comprise at least one pretreatment method, such as: prehydrolysis of the lignocellulose-containing material, steam explosion of the lignocellulose-containing material, alkaline treatment, solvent extraction, partial hydrolysis of the lignocellulose-containing material, and extraction of the lignocellulose-containing material.

The lignocellulose-containing material can comprise at least one lignocellulosic material, such as cellulose, hemicellulose, or lignin. The xylan-containing matter can comprise one or more of the following: wood, hardwood as alder, aspen, birch, beech, eucalyptus, poplar, willow, softwood as pine and spruce, plants, plant constituents, grain as wheat, barley, rye, rice and oat, particulates of grain as straw, hulls, husks, fiber, stems, shells, corn cobs, cornstraw, corn fiber, nutshells, almond shells, coconut shells, bagasse, cotton seed bran, cotton seed skins, wood chips, sawdust, woodpulp, processed paper, spent sulphite liquor, spent liquor from paper processing, spent liquor from woodpulp processing, sulphite cooking liquor, or liquids derived from any of the preceding.

The hydrolyzed solution can comprise biomass hydrolysates. The biomas hydrolysates can be obtained by: direct acid hydrolysis of the biomass, enzymatic prehydrolysate obtained by prehydrolysis of the biomass with steam or acetic acid, acid hydrolysis of prehydrolysate obtained by prehydrolysis of the biomass with steam or acetic acid, or a sulphite pulping process. The biomass hydrolysates can also comprise or be derived from: spent sulphite pulping liquor, acid spent sulphite liquor, spent liquor from softwood pulping before hexoses are removed, spent liquor from softwood pulping after hexoses are removed, spent liquor from hardwood pulping, spent liquor from digestion of the biomass, spent liquor from hydrolysis of the biomass, spent liquor from solvent-based pulping, spent liquor from phenol based pulping, spent liquor from formic acid based pulping, spent liquor from ethanol-based pulping, mother liquor from crystallization of xylose, and diluted runoff of xylose crystallization of sulphite spent pulping liquor based fraction.

The pentose can comprise at least one pentose-containing material, such as xylose or arabinose. During fermentation, arabinose in the processed solution can be reduced to arabinitol. The hexose can comprise at least one hexose-containing material, such as: glucose, galactose, rhanmose, mannose, or other monosaccharides.

The microbes used to ferment the hydrolyzed solution can comprise at least one fermenting microorganism, such as: naturally occurring bacteria, recombinant bacteria, naturally occurring yeast, recombinant yeast, or fungi. The naturally occurring bacteria can comprise: *Bacillus macerans* DMS 1574, *Bacteroides polypragmatus* NRCC 2288, *Clostridium saccharolyticum* ATCC 35040, *C. thermohydrosulfurcium* 39E, *C. thermohydrosulfurcium* ATCC 31925, *Erwinia chrysanthemi* 8374, *Thermoanaerobacter ethanolicus* ATTC 31938, *Lactobacillus brevis*, or *Lacococcus lactis ssp. Lactis*. The recombinant bacteria can comprise: *Erwinia chrysanthemi* 8374, *Escherichia coli* B, *E. coli* B K011, *Kiebsielle oxytoca* M5A1, *K. planticolsa* SDF20, *Zymomonas mobilis* CP4, or *Z. mobilis* NRRL, 14023.

The naturally occurring yeast can comprise: *Candida blanki* ATCC 18736, *C. acidothermophilum* ATCC 20831, *C. brassicae* ATCC 32196, *C. famata*, *C. fructus* JCM 1513, *C. guluilliermondil* ATCC 22017, *C. shehatae* CBS 4705, *C. shehatae* CSIR Y492 (also CBS 2779 and ATCC 60778), *C. shehatae* ATCC 22984 sp CSIR 62 A/2, *C. tenius* CBS 4435, *C. tropicalis* KY 5014, *C. tropicalis* ATCC 20240, *C. tropicalis* ATCC 9968, *C. tropicalis* NRRL y 11860, *Clavispora* sp. UWO 83-833-1, *Kluyveromyces cellobiovous* KV 5199, *K. marxianus*, *Pachysolen tannophilus* NRRL Y 2460 (also ATCC 32691), *P. tannophilus* RL 171, *Pichia segobiensis* CBS 6857, *P. stipitis* CBS 5773, *P. stipitis* CBS 5776, *P. stipitis* NRRL Y 1714, *Schizosaccharomyces pombe* ATCC 2478, *Hansenula anomala* ATCC 34080, *Kluyveromyces fragilitis* ATCC 12424, *Saccharomyces uvarum* ATCC 24556, *S. uvarum* ATCC 26602, *F. oxysporum*, or *Debaryomyces hansenii*. The recombinant yeast can comprise *Saccharomyces cerevisiae*, *S. cerevisiae* TJ 1, *S. cerevisiae* H550, *S. cerevisiae* ATCC 24860, *Schizosaccharomyces pombe* ATCC 2456, or *S. pombe* NRRL Y164.

The fungi can comprise: *Aureobasidium pullulans*, *Fusarium avenaceium* VTT-D-80146, *F. clamydosporum* VTT-D-77055, *F. culmorum* VTT-D-80148, *F. graminearum* VTT-D-79129, *F. lycopersici* ATCC 15417, *F. oxysporum* VTT-D-80134, *F. sembucium* VTT-D-77056, *F. solani* VTT-D-80139, *Monilia sp.*, *Mucor sp.* 105, *Neurospora crassa* NCIM870, or *Paeceilmyces* sp. NFI ATCC 20766.

Preferably, the fermenting microorganism is a yeast of the genera *Candida*, *Pichia*, *Pachysolen*, or *Debaryomyces*, such as: *Candida tropicalis*, *Candida tropicalis* strain having accession number ATCC 9968, which is available from The American Type Culture Collection (ATCC), 10801 University Boulevard, Manassas (VA), 20110-2209, U.S.A., *Pachysolen tannophilus* NRRL Y-2460, which is available from the Microbial Genomics and Bioprocessing Research Unit, National Center for Agricultural Utilization Research, 1815 N. University Street, Peoria, Ill. 61604, U.S.A. and is also available from the ATCC under ATCC accession number 32691, *Candida shehatae* CBS 2779, which is available from The Centraalbureau voor Schimmelcultures (CBS)—an institute of the Royal Netherlands Academy of Arts and Sciences, Uppsalalaan 8, 3584 CT Utrecht, The Netherlands, whose postal address is P.O. Box 85167, 3508 AD Utrecht, The Netherlands and is also available from the ATCC under ATCC accession number 60778, *Pachysolen tannophilus* NRRL Y-2460, the ATCC under accession number32691 or *Debaryomyces hansenii* ATCC 10620, which is available from the ATCC.

Fermenting can occur at a temperature ranging from about 10 to about 45 degrees C. at a pH ranging from 4 to 7 with a yeast concentration of about 1 to about 40 g of dry yeast per liter of processed solution for about 24 to about 96 hours in the presence of at least one nutrient. The nutrient can comprise: a yeast extract, diammoniumphosphate, peptone, biotin, thiamin, folic acid, a water soluble vitamin, a fat soluble vitamin, vitamin A, vitamin B complex, vitamin D, vitamin E, vitamin K, vitamin B1, vitamin B2, vitamin B5, vitamin B6, vitamin B12, vitamin B15, or another vitamin.

Another method of processing lignocellulose-containing material from xylan-containing matter in biomass comprising pentose and hexose, can comprise partially hydrolyzing the lignocellulose-containing material from xylan-containing matter in biomass comprising pentose and hexose to produce a partially hydrolyzed solution comprising free pentoses and hexoses, pentosans, and hexosans. The partially hydrolyzed solution can be separated into an extracted biomass and solubles, the extracted mass comprising hexosans as glucans, and solids as lignin and cellulose, the solubles comprising pentoses, hexoses, soluble pentoses and hexosans, and residue.

The extracted biomass can be hydrolyzed to produce a hydrolyzed biomass comprising hydrolyzed hexoses, hydrolyzed pentoses, and hydrolyzed solids. During hydrolysis, a substantial amount of the pentosans can be converted to pentoses, and a substantial amount of the hexosans can be converted to hexoses. The hydrolyzed biomass can be separated into solids comprising lignin and a separated biomass solution comprising pentoses and hexoses. The separated biomass solution can comprise a greater concentration of pentoses by weight on a dry substance (solids) basis than the hydrolyzed pentoses in the hydrolyzed biomass. Furthermore, the separated biomass solution can comprise a greater concentration of hexoses by weight on a dry substance (solids) basis than the hydrolyzed hexoses in the hydrolyzed biomass. Also, the separated biomass can comprise a greater concentration of solids by weight on a dry substance (solids) basis than the hydrolyzed solids in the hydrolyzed biomass.

The solubles can be fractionated to separate the solubles into fractions comprising a xylose-rich fraction, a xylose-containing fraction, a recycle fraction, and a residue (residual) fraction. The xylose-rich fraction can comprise a higher concentration of xylose by weight on a dry substance (solids) than the xylose in the solubles. The residue fraction can comprise a higher concentration of residue by weight on a dry substance (solids) than the residue in the solubles. Furthermore, the xylose-rich fraction can comprise a higher concentration of at least one compound, such as consisting of xylose, arabinose, mannose, or galactose and rhamnose, by weight on a dry substance (solids) than the compound in the other fractions.

The xylose-rich fraction can be reduced, such as by chemical hydrogenation or biochemical hydrogenation, to produce reduced xylitol. Before reduction xylose fraction can be purified e.g. ion exchange. The hydrogenated xylitol can have a greater concentration of xylitol by weight on a dry substance (solids) basis than the xylitols in the solubles.

The xylose-containing fraction and the separated biomass solution can be fermented with microbes to produce a fermented solution comprising fermented ethanol and spent microbes. During fermentation of the xylose-containing fraction and the separated biomass solution, a substantial amount of the xylose in the xylose-containing fraction can be reduced to fermented ethanol and/or xylitol and/or a substantial amount of the pentoses and hexoses in the separated biomass solution can be converted to fermented ethanol. Arabinose in the separated biomass can be reduced to arabinitol during fermentation. Fermented liquid derived from the fermented solution can be distilled to produce a distilled solution comprising distilled ethanol. The distilled ethanol can comprise a greater concentration of ethanol by weight on a liquid basis than the fermented ethanol in the fermented solution.

A substantial portion of the spent microbes from the fermented solution can be separated, such as by filtration, centrifugation, and decanting, prior to the distilling to produce the fermented liquid derived from the fermented solution. The fermented liquid can comprise fermented ethanol and some spent microbes. The fermented liquid can comprise substantially less spent microbe&. by weight on a dry substance (solids) basis that the spent microbes in the fermented solution.

Separation of the hydrolyzed biomass can be accomplished by at least one separation method, such as: filtration of the hydrolyzed biomass, membrane filtration of the hydrolyzed biomass, ultrafiltration of the hydrolyzed biomass, nanofiltration of the hydrolyzed biomass, microfiltration of the hydrolyzed biomass, centrifugation of the hydrolyzed biomass, decanting of the hydrolyzed biomass, crystallization of the hydrolyzed biomass, chromatography, ion-exchange of the hydrolyzed biomass, concentration of the hydrolyzed biomass, evaporation of the hydrolyzed biomass, reverse osmosis of the hydrolyzed biomass, color removal of the hydrolyzed biomass, reduction of the hydrolyzed biomass, detoxification of the hydrolyzed biomass, and catalytic hydrogenation of the hydrolyzed biomass.

The separated biomass solution and/or the xylose-containing fraction, can be detoxified to help remove inhibitors prior to fermenting with one or more of the following: liming, calcium hydroxide addition, calcium oxide addition, sodium hydroxide addition, pH adjustment, activated charcoal treatment, extraction with organic solvents, ion exchange, ion exclusion, molecular sieves, steam stripping, heating, removing furhral, stripping volatile compounds, and reduction of the separated biomass solution by sulphite addition.

If desired, at least some of the solids in the extracted biomass can be burned (combusted or incinerated). Residue after total hydrolysis containing lignin can be used as binder or disintegrant.

The solubles can be fractionated by chromatographic separation, such as by: batch separation, continuous simulated moving bed separation, or sequential simulated moving bed separation. The solubles can also be fractionated by filtering the solubles, such as by: membrane filtration, ultrafiltration, nanofiltration, or microfiltration. Filtering can comprise passing a solution comprising the solubles through at least one membrane, such as: a high shear membrane, a vibrating membrane, a rotating membrane, a flat sheet membrane, a tubular membrane, a spiral membrane, a hollow fiber membrane, a neutral charged membrane, an ionic membrane, a cationic membrane, and an anionic membrane.

The hydrogenated fraction can be crystallized to produce xylitol crystals. Crystallization can be accomplished by different methods, e.g. cooling crystallization The xylitol crystals can be separated e.g. by centrifugation or filtration and washed with water to produce substantially pure crystalline xylitol.

Hydrolysis of the extracted biomass can be accomplished by enzymes having a cellulolytic and hemicellulolytic e.g. xylanolytic activity to hydrolyze the extracted biomass, or acid hydrolysis of the extracted biomass or by autohydrolysis using water or steam.

Partially hydrolyzing of the lignocellulose-containing material can be accomplished by: steam explosion of the lignocellulose-containing material, partial enzymatic hydrolysis of the lignocellulose-containing material with enzymes having a cellulolytic and hemicellulolytic e.g. xylanolytic activity to partially hydrolyze the lignocellulose-containing material, and partial acid hydrolysis of the lignocellulose-containing material, or subjecting the lignocellulose-containing material to acetic acid.

The partially hydrolyzed solution can be separated and/or clarified by at least one separation method selected from the group consisting of: centrifugation of the partially hydrolyzed solution, decanting of the partially hydrolyzed solution, crystallization of the partially hydrolyzed solution, precipitation as $CaSO_4$-precipitation, chromatography of the partially hydrolyzed solution, ion-exchange, concentration of the partially hydrolyzed solution, evaporation of the partially hydrolyzed solution, reverse osmosis of the partially hydrolyzed solution, filtration of the partially hydrolyzed solution, membrane filtration of the partially hydrolyzed solution, ultrafiltration of the partially hydrolyzed solution, nanofiltration of the partially hydrolyzed solution, or microfiltration of the partially hydrolyzed solution.

As previously indicated, the partially hydrolyzed solution can comprise biomass hydrolysates. The biomass hydrolysates can comprise: spent sulphite pulping liquor, acid spent sulphite liquor, spent liquor from hard wood pulping, spent liquor from softwood pulping before hexoses are removed, spent liquor from softwood pulping after hexoses are removed, spent liquor from digestion of the biomass, spent liquor from hydrolysis of the biomass, spent liquor from solvent-based pulping, spent liquor from phenol based pulping, spent liquor from formic acid based pulping, spent liquor from ethanol-based pulping, mother liquor from crystallization of xylose, and diluted runoff of xylose crystallization of sulphite spent pulping liquor based liquor.

The microbes used to ferment the xylose-containing fraction and the separated biomass solution can comprise at least one fermenting microorganism, such as: naturally occurring bacteria, recombinant bacteria, naturally occurring yeasts, recombinant yeasts, or filamentous fungi. As previously indicated, the naturally occurring bacteria can comprise: *Bacillus macerans* DMS 1574, *Bacteroides polypragmatus* NRCC 2288, *Clostridium saccharolyticum* ATCC 35040, *C. thermohydrosulfurcium* 39E, *C. thermohydrosulfuricum* ATCC 31925, *Erwinia chrysanthemi* 8374, *Thermoanaerobacter ethanolicus* ATTC 31938, *Lactobacillus brevis*, or *Lacococcus lactis ssp. Lactis*. The recombinant bacteria can comprise: *Erwinia chrysanthemi* 8374, *Escherichia coli* B, *E. coli* B K011, *Klebsiella oxytoca* M5A 1, *K. planticola* SDF20, *Zymomonas mobilis* CP4, or *Z. mobilis* NRRL 14023. The naturally occurring yeasts can comprise: *Candida blanki* ATCC 18736, *C. acidothermophilum* ATCC 20831, *C. brassicae* ATCC 32196, *C. famata*, *C. fructus* JCM 1513, *C. guillievmondii* ATCC22017, *C. shehatae* CBS 4705, *C. shehatae* CSIR Y492, *C. shehatae* ATCC 22984. sp CSIR 62 A/2, *C. tenuis* CBS 4435, *C. tropicalis* KY 5014, *C. tropicalis* ATCC 20240, *C. tropicalis* ATCC 9968, *C. tropicalis* NRRL y 11860, *Clavispora* sp. UWO 83-833-1, *Kluyveromyces cellobiovous* KV 5199, *K. marxianus*, *Pachysolen tannophilus* NRRL Y 2460, *P. tannophilus* RL 171, *Pichia segobiensis* CBS 6857, *P. stipitis* CBS 5773, *P. stipitis* CBS 5776, *P. stipitis* NRRL Y 1714, *Schizosaccharomyces pombe* ATCC 2478, *Hansenula anomala* ATCC 34080, *Kluyveromyces fragilis* ATCC 12424, *Saccharomyces uvarum* ATCC 24556, *S. uvarum* ATCC 26602, *F. oxysporum*, or *Debaryomyces hansenii*. The recombinant yeast can comprise: *Saccharomyces cerevisiae, S. cerevisiae* TJ1, *S. cerevisiae* H550, *S. cerevisiae* ATCC 24860, *Schizosaccharomyces pombe* ATCC 2456, or *S. pombe* NRRL, Y164. The fungi can comprise: *Aureobasidium pullulans, Fusarium avenaceium* VTT-D-80146, *F. clamydosporum* VTT-D-77055, *F. culmorum* VTT-D-80148, *F. graminearum* VTT-D-79129, *F. lycopersici* ATCC 15417, *F. oxysporum* VTT-D-80134, *F. sembucium* VTT-D-77056, *F. solani* VTT-D-80139, *Monilia* sp., *Mucor* sp. 105, *Neurospora crassa* NCIM 870, or *Paecilomyces* sp. NFI ATCC 20766.

Preferably, the microbes used to ferment the xylose-containing fraction and the separated biomass solution is a yeast of the genera *Candida, Pichia, Pachysolen*, or *Debaryomyces*, such as: *Candida tropicalis, Candida tropicalis* strain having an accession number ATCC 9968, *Pachysolen tannophilus*, or *Debaryomyces hansenii*.

Fermentation of the xylose-containing fraction and the separated biomass solution can occur at a temperature ranging from about 10 to about 45 degrees C at a pH ranging from 4 to 7 with a yeast concentration of about 1 to about 40 g of dry yeast per liter of solution comprising the xylose-containing fraction and the separated biomass solution, for about 24 to about 96 hours in the presence of at least one nutrient. The nutrient can comprise: a yeast extract, diammoniumphosphate, peptone, biotin, thiamin, folic acid, a water soluble vitamin, a fat soluble vitamin, vitamin A, vitamin B complex, vitamin D, vitamin E, vitamin K, vitamin B1, vitamin B2, vitamin B5, vitamin B6, vitamin B12, vitamin B15, or another vitamin.

Different methods of detoxification, i.e., the removal of inhibitors from xylose containing fraction can increase their fermentability. The addition of activated charcoal, extraction with organic solvents, ion-exchange, ion exclusion, molecular sieves, liming, and/or steam stripping, can be used to remove inhibitors. Liming can also be used as a detoxification method and can be implemented in various ways. Calcium hydroxide or some other hydroxide can be added to the medium until the pH reaches 8.5-10.5. After mixing, the resulting precipitate can be removed. The precipitate can comprise mainly calcium salts of low solubility dominated by calcium sulfate or organic or inorganic anions This treatment can be combined with heat, because at elevated temperatures the solubility of calcium sulfate decreases. Volatile compounds, such as furfural, can be stripped off. Calcium sulfate precipitates acidic compounds. Sulfite is often added at some stage of the detoxification before or after overliming. Sulfite functions as a reducing agent.

The invention is described in further detail by means of the following examples, which are not intended to restrict the invention.

EXAMPLE 1

Production of Ethanol and Xylitol from Birch Chip

A steam explosion treatment was carried out on birch chips at 215 degrees C. with a delay time of 4.5 minutes. The apparatus used is commercially available (Stake Technology, Canada).

30 kg of chips pretreated by steam explosion were suspended in 400 l of water at 50 degrees C. in a reactor furnished with stirring means. The pH of the suspension was regulated to 4.8 with a NaOH solution. The following enzymes were added into the reactor:

| | |
|---|---|
| Cellulase Multifect ® (cultor) | L 250 4 FPU/g d.s. |
| Beta-Glucosidase Novozyme ™ (Novo) | 188 5 IU/g d.s. |
| Hemicellulase Multifect ® K (Cultor), containing xylanase | 18 U/9 d.s. |
| 6-xvlosidase | 9 nkat/g d.s. |
| esterase | 2 nkat/g d.s. |

The reaction was started, and after three and six hours pretreated birch chips were added to the mixture to increase the solids content to 14% by weight. The hydrolysis was continued for three days at 50 degrees C. and at a pH of 4.8. The yield after the hydrolysis was 16% of glucose and 12% of xylose on the dry weight of the pretreated chips.

The solution was separated from the dry solids in a decanting centrifuge (Sharples P 600). The finely powdered matter was removed in a Westfalia Na7-06-076 separator, and the xylose-glucose solution was concentrated by evaporation. The pH of the concentrate was 5. 1, and the composition are shown in Table 1:

TABLE 1

| | |
|---|---|
| Glucose | 10.3% |
| Xylose | 7.6% |
| Other monosaccharicles | 3.1% |
| Oligosaccharides | 5.5% |

The total solids content was about 32%.

The solution additionally contained salts of organic acids and small amounts of lignin decomposition products, furfural, phenols and other organic substances.

The hydrolyzed product was fermented with the yeast Candida tropicalis ATCC 9968. A New Brunswick Scientific Co If 250 fermentor was used, whereto gas analysis and mass spectrometric apparatus was connected.

The fermentation solution is shown in Table 2:

TABLE 2

| | |
|---|---|
| 60 l | prehydrolysate (dry solids content about 32%) |
| 1.5 kg | Gistex yeast extract (steam sterilized at 121 degrees C., 15 min.) |
| 29 l | water |

The inoculation cultures were grown in two stages, first in a 2 l Erlenmeyer flask in an Orbital Shaker at 30 degrees C. for 2 days, and then in a Microgen TM SF 116 laboratory fermentor having an operating volume of 11 l. The fermentor was aerated at a rate of 5.5 Nl/min. (0.5 VVM) and stirred at a rate of 500 rpm. The culturing lasted for one day.

The actual fermentation was performed on a pilot scale, the operating volume being 100 l. The fermentor was aerated at a rate of 20 Nl/min. (0.2 VVM) and stirred at a rate of 100 rpm. The temperature was maintained at 30 degrees C. and the pH at 6. Plurior® was used as an antifoaming agent.

The fermentation results are shown in Table 3.

TABLE 3

| Time (h) | Yeast (g/kg) | Xylitol (g/l) | Glucose (g/l) | Ethanol (g/l) |
|---|---|---|---|---|
| 0 | 2.0 | 0.0 | 53.5 | 1.9 |
| 16 | 6.1 | 2.9 | 2.4 | 26.4 |
| 23.5 | | 4.7 | | 26.7 |
| 41.0 | 7.4 | 9.0 | 1.9 | 25.6 |
| 65.0 | 8.0 | 15.8 | | 24.9 |
| 91.5 | 6.1 | 21.2 | | 23.4 |
| 136 | | 20.6 | | 22.3 |

After the fermentation, substantially all sugars had converted into xylitol and ethanol. Ethanol was recovered from the solution by distilling the fermented solution in a conventional manner. The distillation apparatus was constructed of standard components (Coming Process Systems) which were of borosilicate glass, and the apparatus comprised equipment for 15 separation steps as follows: boiler, 13 bubble plates and a feed plate between the fourth and fifth bubble plates seen from the top. The diameter of the column was 10 cm.

The distillation was carried out at a pressure of 110 mbar at a feed rate of 10 l/h and with a reflux ratio of 3:1. 110 l of fermenting solution gave 7.0 kg of distillate which contained 27.1% by weight of ethanol. The ethanol content of the bottom product was 0.02% by weight.

The separation and, if desired, crystallization of xylitol were carried out as described in Examples 2 and 3.

EXAMPLE 2

Production of Ethanol and Xylitol from Sulphite Spent Liquor

The starting material used was a sugar fraction chromatographically separated from a sulphite spent liquor (Finnish Patent Application 862273, U.S. Pat. No. 4,631,129), containing a considerable amount of hexoses, mainly glucose. The composition of the solution prior and subsequent to fermentation is shown in Table 4.

TABLE 4

| ingredient | Before fermentation | after fermentation |
|---|---|---|
| dry solids, % by weight | 19.0 | — |
| oligosacch., % of dry solids | 14.8 | 10.3 |
| glucose | 90.0 | 1.4 |
| xylose | 42.0 | 3.5 |
| arabinose | 5.0 | 2.3 |
| xylitol | — | 25.4 |
| ethanol | | 42.0 |
| arabinitol | | 2.8 |

The fermentation was carried out with a *Debaryomyces hansenii* strain, and 3 g/l of yeast extract, 3 g/l of malt extract and 5 g/l of peptone were added. The pH of the solution to be fermented was initially about 6.0, the temperature was about 30 degrees C. and the fermentation was carried out in an Orbital Shaker (200 rpm).

The ethanol produced in the fermentation was recovered by distillation (50 degrees C., 200 mbar), and a chromatographic separation was carried out on the remaining solution in a column filled with a divinylbenzene-cross-linked polystyrene-based cation exchange resin, in which connection the conditions shown in Table 5 were used.

TABLE 5

| | | |
|---|---|---|
| height of column | 4.0 | m |
| Diameter of column | 22.5 | cm |
| temperature | 65 | ° C. |
| flow rate (H 2 0) | 30 | l/h |
| feed concentration | 30 | % by weight |
| feed volume | 6 | kg of solid matter |
| resin: $^{Finex\ TM}$ C 09 | | |
| Particle size | 0.37 | MM |
| ionic form | Na | |

The results have been graphically presented in FIG. 1. Xylitol was separated from xylose and the other impurities, and recovered from the xylitol-rich fraction, wherefrom pure xylitol was crystallized in the manner described in Example 3.

EXAMPLE 3

Crystallization of Xylitol

Xylitol was crystallized from a chromatographically enriched xylitol solution containing 82.5% of xylitol on dry solids by evaporating the solution to 92% by weight of dry solids at 65 degrees C. Into a solution of a natural weight of 2,200 g, xylitol crystals of about 0.04 mm were inoculated in an amount of 0.03% by weight, and the solution was cooled in 55 hours to 45 degrees C. in accordance with the following empirical equation:

$$T=T1-(t/t1)**2*(T2-T2),$$

wherein
T=temperature of solution, degrees C.
T1=seeding temperature (65 degrees C.)
T2=final temperature (45 degrees C.)
t=time from seeding, h
t1=crystallization time (55 h)

The crystallization was carried out in a 2 l pilot crystallizer furnished with a vertical stirrer. 65% of the xylitol present in the solution crystallized as raw crystals which were separated from the mother solution in a basket centrifuge (Hettich, Roto Silenta TM 11).

During the centrifugation, the crystals were washed with water (4% of water on the weight of the crystals). The centrifugation time was 5 minutes, and a centrifugal force of 2000 g was used. 1,510 g of natural weight of a crystal suspension was centrifuged, which gave 705 g of crystalline dry solids having a xylitol content of 99.4% of dry solids. The average size of the crystals was 0.37 mm and the standard deviation 24%.

The raw crystals can be recrystallized, into product crystals by e.g. the method disclosed in Finnish Patent 69 296.

EXAMPLE 4

Production of Ethanol and Xylitol from Barley Hulls

Barley hull mass having the carbohydrate composition in Table 6 was used as a starting material.

TABLE 6

| xylan | 21.6% of dry solids |
|---|---|
| glucan | 33.4 |
| araban | 5.7 |
| galactan | 1.4 |
| mannan | 0.6 |
| rhamnan | 0.2 |

The barley hull mass was hydrolyzed at a pressure of 2.4 MPa (350 psi) at 235 degrees C., and the delay time was 2.0 minutes. The hydrolyzed material contained 45.6% of dry solids, and the content of dissolved solids was 34.2% on dry solids. The filtrate contained 12.7% of monosaccharides, 16.9% of acetic acid and 0.5% of furfural calculated on a dry solids basis. Posthydrolysis was carried out on the filtrate by adjusting the pH to 1 with sulphuric acid and by hydrolyzing the solution for 4 hours at a pressure of 101 kPa (one atmosphere) at 100 degrees C. The composition of the posthydrolysate is shown in Table 7.

TABLE 7

| oligosaccharides | 1.39% | of dry solids |
|---|---|---|
| monosaccharides | 45.2% | |
| xylose | 67.3% | of the monosaccharides |
| arabinose | 11.4% | |
| glucose | 16.0% | |
| galactose | 3.3% | |
| mannose | 1.5% | |
| rhamnose | 0.5% | |
| others (e.g. furfiral) | 3.3% | of dry solids |

The fermentation of the posthydrolysate, the recovery of ethanol and the crystallization of xylitol were carried out as described in the preceding examples.

EXAMPLE 5

Production of Ethanol and Xylitol from Oat Hulls

Oat hull mass having the carbohydrate composition in Table 8 was used as a starting materials.

TABLE 8

| xylan | 26.5% of dry solids |
|---|---|
| glucan | 30.7% |
| araban | 3.0% |
| galactan | 1.3% |
| mannan | 0.2% |

The oat hull mass was hydrolyzed at a pressure of 2.4 MPa (350 psi) at 235 degrees C., and the delay time was 2.0 minutes. The hydrolyzed material contained 39.1% of dry solids, and the content of dissolved solids was 36.4% of dry solids. The filtrate contained 12.0% of monosaccharides, 12.9% of acetic acid and 0.5% of furfural calculated on dry solids. Posthydrolysis was performed on the filtrate by adjusting the pH to 1 with sulphuric acid and by hydrolyzing the solution for 4 hours at a pressure of 101 kPa (one atmosphere) at 100 degrees C. The composition of the posthydrolysate is shown in Table 9:

TABLE 9

| oligosaccharicles | 1.3% | of dry solids |
|---|---|---|
| monosaccharides | 63.1% | |
| xylose | 69.0% | of the monosaccharicles |
| arabinose | 6.9% | |
| glucose | 19.1% | |
| galactose | 3.1% | |
| mannose | 0.8% | |
| rhamnose | 1.1% | |
| Others (e.g. furfural) | 2.8% | of dry solids |

The fermentation of the posthydrolysate, the recovery of ethanol and the crystallization of xylitol were carried out as described in the preceding examples.

EXAMPLE 6

Steam Explosion and Extraction of Birch

A steam explosion treatment was carried out on birch chips with a factory-scale equipment at a temperature of 215 degrees C. with a delay time of 4.5 minutes. The manufacturer of the equipment used is Technip, type of apparatus Stake II System.

The steam explosion product was suspended in hot process water in a mixing container to produce a fibrous suspension of about 3.5%. Therefrom the slurry was directed via an overflow to form a smooth layer on a 5-phase band filter operating on the countercurrent principle (type A 40-β25; manufacturer Filters Philippe; width of wire 2.7 m; wire supplied by manufacturer of apparatus). The solid mass was further extracted with hot water on the wire. The aqueous solution obtained is shown in Table 10.

TABLE 10

| | |
|---|---|
| dry solids content | 8.7% by weight |
| xylose monomers | 1.1% of natural weight |
| xylose oligomers | 3.7% of natural weight |
| Glucose | 0.04% of natural weight |

EXAMPLE 7

Enzymatic Degradation of Steam-exploded Water-washed Birch Chip Mass

The composition of the steam-exploded (215 degrees C./4.5 min.) birch chip mass (prepared in accordance with Example 6) used as raw material for the hydrolysis is shown in Table 11.

TABLE 11

| | |
|---|---|
| dry solids | 32% |
| cellulose | 60% of dry solids |
| xylan | 3.6% of dry solids |
| lignin (extractable in acetone) | 25% of dry solids |
| Klason lignin | 12.3% of dry solids |

90 kg of the above-described mass was weighed into a reaction vessel provided with a stirrer and a heating jacket and containing 370 l of water. The mixture was heated to 50 degrees C., the pH was adjusted to 4.8-5.0, whereafter the enzyme solutions were added (1.24 l of Multifect® L 250, 0.11 l of Novozyme™ 9188 and 0.09 l of Multifect® K). As activity units, the added quantities correspond to 6 FPU/g of cellulase, 5 IJ/g of beta—glucosidase and 0.02 ml of growth solution/g of mass dry solids of hemicellulase (18 U/g of dry solids of xylanase, 9 nkat/p of dry solids of 13-xylosidase, 2 nkat/g of dry solids of esterase). The reaction was allowed to continue under the conditions described above for 18 hours. Thereafter mass and enzymes were added in the same quantities as in the starting phase. A corresponding mass and enzyme addition was repeated after 21 hours from the start. Thereafter the hydrolysis reaction was allowed to continue so that the total time was 40 hours. The enzyme action was then stopped by heating the mass mixture to 80 degrees C. for 10-20 minutes. In that connection, the remaining solid matter was solidified and thereby made easier to separate. The solid matter and the solution were separated from one another by centrifugation (Pennvalt Sharples P600 model). The solution was further clarified by separating the remaining fine precipitate in a separator (Westfalia model NA7-06-076). The solution was concentrated to 33% DS for fermentation by evaporating with a Luwa evaporator in vacuo at a temperature of 40-50 degrees C.

Hydrolysis yields of steam exploded, water washed birch chip mass in enzyme treatment are shown in Table 12.

TABLE 12

| | % in solution | yield % of dry solids | conversion % |
|---|---|---|---|
| glucose | 3.3 | 24.5 | 40.8 |
| xylose | 0.4 | 2.6 | 72.0 |
| oligosacchariles | 0.7 | | |

Composition of the clarified and evaporated enzyme hydrolysate solution are shown in Table 13.

TABLE 13

| | |
|---|---|
| glucose | 22.7% of natural weight |
| xylose | 2.7% of natural weight |
| oligosacchariles | 4.7% of natural weight |

EXAMPLE 8

Fermentation of Enzymatic Hydrolysate of Steam Exploded, Water Washed Birch Chip Mass into Ethanol The hydrolyzed cellulose was fermented with a yeast Candida tropicalis ATCC 9968. A New Brunswick Scientific IF-250 fermentor was used.

The fermentation solution is shown in Table 14.

TABLE 14

| | |
|---|---|
| 45 l | hydrolysate |
| 1.5 kg | Gistex yeast extract |
| 40 l | water |

The inoculation cultures were grown in two steps, first in a 2 l Erlenmeyer flask in an Orbital Shaker at 30 degrees C. for 2 days, then in a New Brunswick Scientific SF-1 16 laboratory fermentor having an operating volume of 11 l. The fermentor was aerated 5.5 Nl/min. (0.5 vvm) and stirred at a rate of 500 rpm. The culturing lasted for one day.

The actual fermentation was carried out on a pilot scale, the operating volume being 100 l. The fermentor was aerated 25 Nl/min (0.25 vvm) and stirred at a rate of 100 rpm. The temperature was adjusted to 30° C., and the foam was controlled, with Plurior antifoaming agent.

The results of the fermentation are set forth in Table 15.

TABLE 15

| time (h) | cell mass (g/l) | glucose (g/l) | ethanol (g/l) |
|---|---|---|---|
| 0 | 1.8 | 105.0 | 1.9 |
| 19.5 | 11.3 | 0 | 51.2 |
| 52 | — | 0 | 48.1 |
| 66 | | 0 | 45.0 |

In the course of 29.5 hours, the yeast consumed all of the glucose in the substrate, producing ethanol therefrom with a yield of 48%.

After fermentation, the yeast cells were separated from the solution by centrifugation (Westfalia NA7-06-076). The clarified solution was distilled to recover the ethanol.

EXAMPLE 9

Recovery of Ethanol from the Fermentation Product of Enzymatic Hydrolysate of Steam Exploded Water Washed Birch Chip Mass 100 litres of fermented cellulose hydrolysate were distilled. The fermentation had been carried out in the manner described in Example 8 and clarified by centrifugation in a Westfalia NA7-06-076 separator. The ethanol content of the solution was 3.4%.

The distillation apparatus was constructed of standard components by Coming Process Systems which were of borosilicate glass. The diameter of the column was 10 cm. The apparatus comprised 15 separation steps: boiler, 13 bubble plates and a feed plate between the fourth and fifth bubble plates seen from the top. The distillation was carried out at a pressure of 100 mbar, at a feed rate of 10 l/h and with a reflux ratio of 3:1. 8.5 kg of distillate were recovered, having an ethanol content of 36.0%. The ethanol content of the bottom product was 0.1%.

EXAMPLE 10

Chromatographic Separation of Xylose from Acid Hydrolyzed Barley Hulls

The post hydrolysate solution prepared according to Example 4 was subjected to a chromatographic separation in a chromatographic separation column. Separation was made with a $Na^+$-form separation resin in a pilot chromatographic separation column as a batch process.

The equipment comprised: a feed tank, a feed pump, a heat exchanger, the column, product containers, pipelines and valves for input and output of solutions, eluent water devices, and instruments for the flow control and for the determination of density, conductivity and temperature of the outflow.

The pilot batch separation was made with a strong acid cation exchange resin (manufactured by Finex Oy, Finland) having the cross-linkage degree of 5.5% DVB and the average particle size of 0.35 mm. 1.5 $m^3$ of this resin was put into a pilot batch separation column having a diameter of 0.6 m and regenerated into sodium ($Na^+$)-form.

The temperature of the process was 65 degrees C. and the flow rate was adjusted to 0.7 m/h which was continuously controlled by valve from the bottom of the separation column.

The solution was concentrated to 30 g DS/100 g and the pH of the feed solution was adjusted to pH 5.5 with 50 wt % NaOH solution and filtered with a pressure filter using diatomaceous earth as filter aid.

The feed solution was pumped through the heat exchanger and the feeding device to the top of the resin bed in the column. The feed solution was moved downwards by feeding ion exchanged water to the top of the column. The density and the conductivity of the out coming solution was measured generally continuously and according to this information the outflow was collected and divided into three fractions: residual fraction (containing salts and small amounts of sugars), recycle fraction (containing e.g. glucose, galactose, xylose and arabinose) and xylose-fraction.

Furthermore, the xylose fraction was taken in two different ways:

The xylose fraction was taken as one fraction, which was then fermented into ethanol and xylitol. Composition of fractions while taking xylose fraction as one fraction are shown in Table 16.

The amount of dry substance as well as the contents of xylose and other analyzed sugars of the feed solution and product fractions of the separation are also shown in Table 16. The xylose yield was calculated from the amount of the component in the particular fraction in relation to the total amount of that component in all out-coming fractions.

TABLE 16

Xylose fraction is taken as one fraction
Composition and Yields

| | Feed solution | Residual fraction | Xylose fraction | Recycle fraction |
|---|---|---|---|---|
| fraction dry solids, kg | 36 | 16.9 | 16.4 | 2.7 |
| dry solids content g/100 g | 30 | 7.3 | 12.3 | 7.4 |
| oligosaccharides, % on dry solids | 1.3 | | | |
| Monosaccharides % on dry solids | 45.2 | | | |
| Xylose % on dry solids | 30.4 | 1.8 | 59.9 | 31.0 |
| glucose, % on dry solids | 7.2 | 4.5 | 9.8 | 10.1 |
| arabinose, % on dry solids | 5.2 | 0.4 | 9.4 | 9.1 |
| galactose + rhamnose, % on dry solids | 1.7 | 0.2 | 3.2 | 2.0 |
| mannose, % on dry solids | .07 | 0.1 | 1.2 | 0.8 |
| xylose, yield % | | | 97.1 | |

The xylose fraction was also divided into two fractions;
1. Xylose I-fraction which contained xylose and most of the glucose and
2. Xylose II-fraction which contained most of the xylose and arabinose The xylose I-fraction was fermented into ethanol and xylitol. Xylose of the Xylose II-fraction was crystallized and crystallization run-off was used e.g. for recovery of additional xylose.

The composition of the fractions are shown in Table 17.

The amount of dry substance as well as the contents of xylose and other analyzed sugars of the feed solution and product fractions of the separation are also shown in Table 17. The xylose yield was calculated from the amount of the component in the particular fraction in relation to the total amount of that component in all out-coming fractions.

TABLE 17

Xylose fraction is taken as two fractions: xylose-I and xylose-II
Composition And Yields

| | Feed solution | Residual fraction | Xylose I-fraction | Xylose II-fraction | Recycle fraction |
|---|---|---|---|---|---|
| fraction dry solids, kg | 36 | 15.6 | 7.1 | 10.9 | 2.5 |
| Dry solids content g/100 g | 30 | 7.8 | 8.5 | 13.1 | 7.6 |
| oligosaccharides, % on dry solids | 1.3 | | | | |
| Monosaccharides, % on dry solids | 45.2 | | | | |
| xylose, % on dry solids | 30.4 | 0.6 | 48.1 | 61.9 | 30.1 |
| glucose, % on dry solids | 7.2 | 1.1 | 25.7 | 5.4 | 1.6 |
| arabinose, % on dry solids | 5.2 | 0.5 | 0.0 | 13.4 | 12.9 |
| galactose + rhamnose, % on dry solids | 1.7 | 0.1 | 3.6 | 3.O | 1.4 |
| mannose, % on dry solids | 0.7 | 0.0 | 1.1 | 1.3 | 0.8 |
| xylose, yield % | | | 33.3 | 65.9 | |

EXAMPLE 11

Fermentation of Xylose Fraction with *Candida shehatae*

Fermentation of the xylose fraction, which was taken as one fraction (example 10, Table 16) from the chromatographic separation step was accomplished with *Candida shehatae*.

The xylose fraction from the separation step was sterilized for 15 min at 120 degrees C. and mixed with a separately sterilized nutrient solution. The composition of the final mixture was the following: xylose 60 g/l, glucose 10 g/l, diammoniumphosphate 3 g/l, yeast extract 1 g/l+traces of the other sugars present in the xylose fraction. The mixture was inoculated with an overnight aerobic culture of Candida shehatae CBS 2779 yeast strain produced on MYXP medium (maltose 3 g/l, yeast extract 3 g/l, xylose 20 g/l and peptone 5 g/l). The amount of the inoculum was Vol 01%. The fermentation was performed at oxygen limitation (oxygen transfer rate appr. 4 mmol/h) and at 30 degrees C. After 72 hours fermentation: 24 g/l ethanol and 7 g/l xylitol was analyzed.

EXAMPLE 12

Fermentation of Xylose Fraction with *Pachysolen tannophilus*

Fermentation of the xylose fraction (example 10, Table 16) which was taken as one fraction from the chromatographic separation step was accomplished with *Pachysolen tannophilus*. The fermentation was performed as in the previous example, but *Pachysolen tannophilus* NRRL Y-2460 yeast strain was used instead of *Candida shehatae*. Oxygen transfer rate was appr. 2.5 mmol/h. After 96 hours fermentation 28 g/l xylitol and 18 g/l ethanol was analyzed by HPLC.

EXAMPLE 13

Fermentation of Xylose I Fraction with *Candida shehatae*

Fermentation of the xylose I fraction (Example 10, Table 17) from the chromatographic separation was accomplished with *Candida shehatae*. The xylose fraction I and a nutrient solution were mixed as in the previous examples, producing a composition of 30 g/l xylose, 16 g/l glucose, 3 g/l diammoniumphosphate, 1 g/l yeast extract and traces of other components from the xylose I fraction. Fermentation was carried out anaerobically, but otherwise as in example 10. The composition of the fermentation broth at 80 hours was 19 g/l ethanol and 6 g/l xylitol.

EXAMPLE 14

Nanofiltration of a Spent Sulphite Pulping Liquor as a Pretreatment Step Using Various Membranes at Various pH Values This example illustrates the effect of the membrane and pH on the performance of nanofiltration (filtrations C1, C3, C6 and C8). The liquor to be treated was a diluted runoff of the xylose crystallization of a Mg-based sulphite spent pulping liquor obtained from beechwood pulping, which had been chromatographically purified using an ion exchange resin in $Mg^{2+}$ form. The pH of the solution was adjusted to the desired value (see Table 18) with MgO. Before the nanofiltration, the liquor was pretreated by dilution (filtrations Cl and C3), by filtration through a filter paper (filtration C6) or with MgO dosing combined with filtration through a filter paper (filtrations C7 and C8).

A batch mode nanofiltration was carried out using a laboratory nanofiltration equipment consisting of rectangular cross-flow flat sheet modules with a membrane area of 0.0046 m 2. Both the permeate and the retentate were recycled back to the feed vessel (total recycling mode filtration). The feed volume was 20 liters. During the filtration, the cross-flow velocity was 6 m/s and the pressure was 18 bar. The temperature was kept at 40 degrees C.

Table 18 presents the results of the total recycling mode filtrations. The flux values in Table 18 were measured after 3 hours of filtration. Table 18 shows the dry substance content (DS) in the feed (%), the xylose content in the feed and in the permeate (based on the dry substance content), the permeate flux at a pressure of 18 bar and the flux reduction caused by fouling. The membranes were Desal-5 DK and NTR-7450.

RDS refers to the refractomeric dry substance content expressed as % by weight.

TABLE 18

Nanofiltration of Spent Sulphite Pulping Liquor

| Filtration No., membrane | pH | DS in the feed, w-% | Xylose in feed, % on DS | Xylose permeate, % on RDS | Flux 1/($m^2$h) | Fouling, % |
|---|---|---|---|---|---|---|
| C1, Desal-5-DK | 3.4 | 8.1 | 22.6 | 27.4 | 31 | 1 |
| C6*, Desal-5-DK | 3.4 | 9.7 | 20.3 | 33.5 | 23 | 1 |
| C7*, Desal-5-DK | 5.9 | 8.2 | 21.7 | 55.2 | 58 | 3 |
| C3, NTR-7450 | 3.4 | 7.6 | 24.3 | 29.9 | 25 | 29 |
| C8, NTR-7450 | 6.1 | 8.3 | 21.8 | 34.5 | 43 | 25 |
| C8, Desal-5-DK | 6.1 | 8.3 | 21.8 | 45 | 30 | 1 |

*average value of two membranes

The results of Table 18 show that nanofiltration provides xylose concentrations of 1.5 to 2.5 times those of the feed. When the pH in the feed is high, the xylose content on RDS in the permeate is high for example when pH is 5.9 or 6.1. Furthermore, the flux was improved even to two-fold at higher pH values.

EXAMPLE 15

Pretreatment with Ultrafiltration

Concentration mode ultrafiltrations DU1 and DU2 were carried out using an RE filter (rotation-enhanced filter). In this filter, the blade rotates near the membrane surface minimizing the concentration polarization during the filtration. The filter was a home-made cross-rotational filter. The rotor speed was 700 rpm. In filtration DU1, the membrane was C5F UF (a membrane of regenerated cellulose having a cut-off size of 5000 g/mol, manufacturer Hoechst/Celgard). In filtration DU2, the membrane was Desal G10 (a thin film membrane having a cut-off size of 2500 g/mol, manufacturer Osmonics/Desal).

Concentration mode filtrations were made using a Mg-based sulphite spent pulping liquor obtained from beechwood pulping. The filtration was carried out at a temperature of 35° C. and a pH of 3.6. The results are presented in Table 19.

TABLE 19

Pretreatment with Ultrafiltration of Mg-Based Sulphite Spent Pulping Liquor

| Filtration No. | Membrane | DS in feed, % | Filtration time | Xylose in feed, % on DS | Xylose in permeate, % on RDS |
|---|---|---|---|---|---|
| DU1 | C5F | 14.4 | 1 hour | 16.3 | 23.2 |
| DU1 | C5F | 22.0 | 23 hours | 9.2 | 20.0 |
| DU2 | Desal GI0 | 12.2 | 3 days | 12.7 | 41.6 |

EXAMPLE 16

Nanofiltration

A one-day laboratory-scale experiment where the permeate was collected out was carried out with the same equipment as in Example 14 and are shown in Table 20 below (filtrations DN1 and DN2). The liquor to be treated was a Mg-based sulphite spent pulping liquor obtained from beechwood pulping.

In filtration DN1 of Table 20, the ultrafiltered spent liquor (DU1 using a C5F membrane) was used as the feed solution. The pH of the solution was adjusted to 4.5 using MgO, and the liquor was prefiltered through a filter paper before nanofiltration. Nanofiltration was carried out at a pressure of 19 bar and at a temperature of 40 degrees C.

Filtration DN2 of Table 20 was carried out using the diluted original spent liquor. Its pH had been adjusted to 4.8 and the solution was prefiltered through a filter paper before nanofiltration. The nanofiltration was carried out at a pressure of 17 bar and at a temperature of 40 degrees C. After about 20 hours of filtration, a permeate volume of 5 liters and a concentrate volume of 20 liters were obtained.

Both filtrations DN1 and DN2 of Table 20 were carried out at a cross-flow velocity of 6 m/s. Fouling was about 1% in both filtrations. The nanofiltration membrane in both filtrations DN1 and DN2 in Table 20 was Desal-5 DK.

In each filtration DN1 and DN2 of Table 20, the nanofiltration membrane was pretreated in three different ways: (1) no pretreatment, (2) washing the membrane with ethanol, and (3) washing the membrane with an alkaline detergent. The results are set forth in Table 20:

TABLE 20

Nanofiltration of Mg-Based Sulphite Spent Pulping Liquor

| Filtration | pH | DS in feed, % | Xylose in feed, % on DS | Xylose in permeate, % on RDS (1)/(2)/(3) | Flux, $l/(m^2h)$ at 20 h |
|---|---|---|---|---|---|
| DN1 | 4.5 | 10.7 | 21.1 | 24/35/49 | 14 (19 bar) |
| DN2 | 4.6 | 12.3 | 16.8 | N.A.*/35/34 | 22/32 (17/19 bar) |

*(N.A. = not analyzed)

Although embodiments and examples of this invention have been shown and described, it is to be understood that various modifications, substitutions, and rearrangements of equipment and method (process) steps, as well as the use of various feed solutions, different microbes, and recovery of various products, can be made by those skilled in the art without departing from the novel spirit and scope of this invention.

We claim:

1. A method of processing lignocellulose-containing material from xylan-containing biomass comprising pentoses and hexoses to produce ethanol and xylitol, comprising the steps of
   hydrolyzing lignocellulose-containing material from xylan-containing biomass comprising pentoses and hexoses to produce a hydrolyzed solution comprising free pentoses and hexoses;
   said lignocellulose-containing material comprising at least one lignocellulosic material selected from the group consisting of cellulose and hemicellulose,
   said pentoses comprising at least one pentose-containing material selected from the group consisting of xylose and arabinose;
   said hexoses comprising at least one hexose-containing material selected from the group consisting of glucose, galactose, rhamnose and mannose;
   said xylan-containing matter selected from the group consisting of wood, hardwood, softwood, plants, plant constituents, grains, particulates of grains, stems, fiber, shells, corn cobs, corn stems, corn fibers, nutshells, almond shells, coconut shells, bagasse, cotton seed bran, cotton seed skins, wood chips, sawdust, woodpulp, processed paper, spent sulphite liquor, spent liquor from hardwood pulping, spent liquor from paper processing, spent liquor from woodpulp processing and sulphite cooking liquor;
   fermenting said hydrolyzed solution with microbes to produce a fermented solution comprising fermented ethanol, fermented xylitol and spent microbes, said fermenting comprising converting a substantial amount of said hexose in said hydrolyzed solution to fermented ethanol and reducing a substantial amount of said xylose in said hydrolyzed solution to fermented xylitol and fermented ethanol;
   said microbes comprising at least one fermenting microorganism selected from the group consisting of naturally occurring bacteria, recombinant bacteria, naturally occurring yeast, recombinant yeast, and fungi;
   wherein said microbes are capable of converting xylose to ethanol and xylitol, and capable of converting hexoses to ethanol; and
   distilling said fermented solution to produce distilled ethanol and a bottom product comprising xylitol and spent microbes; and
   separating by fractionating said bottom product using a method selected from chromatographic separation and membrane filtration, so as to provide a xylitol enriched fraction, wherein said xylitol enriched fraction comprises a greater concentration of xylitol than does the bottom product, on a dry substance (solids) basis.

2. A method according to claim 1 further including crystallizing said xylitol enriched fraction to produce crystalline xylitol.

3. A method according to claim 1 wherein:
   said hydrolyzed solution is subjected to at least one treatment selected from the group consisting of: pH adjustment, concentration, filtration, filtering with a pressure filter, filtering with diatomaceous earth, chromatographic separation, detoxification, removing inhibitors, calcium hydroxide addition, sodium hydroxide addition, treating with activated charcoal, extraction with organic solvents, ion exchange, steam stripping, heating, removing furfural, stripping volatile compounds, and reduction of said hydrolyzed solution by sulphite addition.

4. A method according to claim 1 wherein:
   said chromatographic separation is selected from the group consisting of batch separation, continuous simulated moving bed separation, and sequential simulated moving bed separation.

5. A method according to claim 1 wherein:
   said membrane filtration is selected from the group consisting of ultrafiltration, nanofiltration, and microfiltration.

6. A method according to claim 5 wherein:
   said membrane is selected from the group consisting of a high shear membrane, a vibrating membrane, a rotating membrane, a flat sheet membrane, a tubular membrane, a spiral membrane, a hollow fiber membrane, a neutral charged membrane, an ionic membrane, a cationic membrane, and an anionic membrane.

7. A method according to claim 2 wherein said crystallization is selected from the group consisting of cooling crystallization, evaporation crystallization, both cooling crystallization and evaporation crystallization, and a combination of cooling crystallization and evaporation crystallization.

8. A method according to claim 7 wherein said xylitol crystals are separated by centrifugation or filtration and washed with water to produce substantially pure crystalline xylitol.

9. A method according to claim 1 further including:
separating a substantial portion of said spent microbes from said fermented solution prior to said distilling;
said separating of said substantial portion of said spent microbes from said fermented solution comprising at least one separating method selected from the group consisting of filtration, centrifugation, and decanting.

10. A method according to claim 1 further including removing a substantial amount of solids from said hydrolyzed solution before fermenting, said removing comprising at least one removal step selected from the group consisting of filtration, centrifugation and decanting.

11. A method according to claim 1 wherein said hydrolyzing is selected from the group consisting of enzymatic hydrolysis of said lignocellulose-containing material with enzymes having a cellulolytic and xylanolytic activity to hydrolyze said lignocellulose-containing material, and acid hydrolysis of said lignocellulose-containing material.

12. A method according to claim 1 further including pretreatment of said lignocellulose-containing material before said hydrolyzing, said pretreatment comprising at least one pretreatment method selected from the group consisting of prehydrolysis of said lignocellulose-containing material, steam explosion of said lignocellulose-containing material, alkaline treatment, solvent extraction, partial hydrolysis of said lignocellulose-containing material, and extraction by alkali, NaOH or $NH_4OH$ of said lignocellulose-containing material.

13. A method according to claim 1 wherein said hydrolyzed solution comprises xylan-containing biomass hydrolysates.

14. A method according to claim 13 wherein said xylan-containing biomass hydrolysates are obtained by a process selected from the group consisting of direct acid hydrolysis, enzymatic hydrolysis, hydrolysis with steam and/or acetic acid, a saprehydrolysis process, autohydrolysis using water or steam, and a sulphite pulping process.

15. A method according to claim 13 wherein said xylan-containing biomass hydrolysates are selected from the group consisting of spent sulphite pulping liquor, acid spent sulphite liquor, spent liquor from hardwood pulping, spent liquor from softwood pulping before hexoses are removed, spent liquor from softwood pulping after hexoses are removed, spent liquor from digestion of said xylan-containing biomass, spent liquor from hydrolysis of said xylan-containing biomass, spent liquor from solvent-based pulping, spent, liquor from phenol based pulping, spent liquor from formic acid based pulping, spent liquor from ethanol-based pulping, mother liquor from crystallization of xylose, and diluted runoff of xylose crystallization of sulphite spent pulping liquor based liquor.

16. A method according to claim 1 wherein:
said pentose in said hydrolyzed solution comprises arabinose; and
said arabinose is reduced to arabinitol during said fermentation.

17. A method according to claim 1 wherein said fermenting microbes are selected from the group consisting of a yeast of the genera *Candida, Pichia, Pachysolen*, or *Debaryomyces*.

18. A method according to claim 17 wherein said yeast is selected from the group consisting of *Candida shehatae* CBS 2779 (ATCC60778), *Candida tropicalis* ATCC 9968 and *Pachysolen tannophilus* NRRL Y-2460 (ATCC32691).

19. A method according to claim 18 wherein said fermenting occurs at a temperature ranging from about 10 to about 45 degrees C. at a pH ranging from 4 to 7 with a yeast concentration of about 1 to about 40 g of dry yeast per liter of hydrolyzed solution for about 24 to about 96 hours in the presence of at least one nutrient.

* * * * *

UNITED STATES PATENT AND TRADEMARK OFFICE
CERTIFICATE OF CORRECTION

| | |
|---|---|
| PATENT NO. | : 7,625,728 B2 |
| APPLICATION NO. | : 11/479654 |
| DATED | : December 1, 2009 |
| INVENTOR(S) | : Eroma et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 518 days.

Signed and Sealed this

Second Day of November, 2010

David J. Kappos
*Director of the United States Patent and Trademark Office*